US007855285B2

(12) United States Patent
Robins et al.

(10) Patent No.: US 7,855,285 B2
(45) Date of Patent: Dec. 21, 2010

(54) METHODS FOR SELECTIVE N-9 GLYCOSYLATION OF PURINES

(75) Inventors: Morris J. Robins, Provo, UT (US); Minghong Zhong, Middletown, MD (US)

(73) Assignee: Brigham Young University, Provo, UT (US)

( * ) Notice: Subject to any disclaimer, the term of this patent is extended or adjusted under 35 U.S.C. 154(b) by 306 days.

(21) Appl. No.: 11/917,544

(22) PCT Filed: Jun. 14, 2006

(86) PCT No.: PCT/US2006/023193

§ 371 (c)(1),
(2), (4) Date: Dec. 14, 2007

(87) PCT Pub. No.: WO2006/138396

PCT Pub. Date: Dec. 28, 2006

(65) Prior Publication Data

US 2008/0207891 A1 Aug. 28, 2008

Related U.S. Application Data

(60) Provisional application No. 60/690,307, filed on Jun. 14, 2005.

(51) Int. Cl.
*C07H 21/00* (2006.01)
(52) U.S. Cl. ............... 536/25.3; 536/25.31; 536/25.32; 536/25.33; 536/25.34
(58) Field of Classification Search ....................... None
See application file for complete search history.

(56) References Cited

U.S. PATENT DOCUMENTS

| 4,189,581 | A | 2/1980 | Scharwaechter et al. |
| 4,495,190 | A | 1/1985 | Hagberg et al. |
| 4,579,849 | A | 4/1986 | MacCoss et al. |
| 4,760,137 | A | 7/1988 | Robins et al. |
| 4,801,710 | A | 1/1989 | MacCoss et al. |
| 5,459,255 | A | 10/1995 | Cook et al. |
| 5,831,092 | A | 11/1998 | Izawa et al. |
| 6,087,497 | A | 7/2000 | Izawa et al. |
| 6,245,910 | B1 | 6/2001 | Izawa et al. |
| 2003/0023078 | A1 | 1/2003 | Montgomery et al. |
| 2004/0039190 | A1 | 2/2004 | Gupta et al. |
| 2004/0110718 | A1* | 6/2004 | Devos et al. ............... 514/45 |

FOREIGN PATENT DOCUMENTS

WO WO 00/75158 A2 12/2000
WO WO 2004/018490 A1 3/2004

OTHER PUBLICATIONS

Alarcon, Karine, et al., "2-Amino-6-(1,2,4-triazol-4-yl)-purine: a useful intermediate in the synthesis of 9-alkylguanines," *Tetrahedron Letters*, 41:7211-7215 (2000).

Džolić, Zoran, et al., "Synthesis, Structural Studes, and Biological Evaluation of Some Purine Substituted 1-Aminocyclopropane-1-carboxylic Acids and 1-Amino-1-hydroxymethylcyclopropanes," *Nucleosides, Nucleotides & Nucleic Acids*, 22(4):373-389 (2003).
Estep, Kimberly G., et al., "Synthesis and Structure—Activity Relationships of 6-Heterocyclic-Substituted Purines as Inactivation Modifiers of Cardiac Sodium Channels," *J. Med. Chem.*, 38:2582-2595 (1995).
International Search Report from corresponding Application No. PCT/US06/23193, dated Jan. 26, 2007 (6 pages).
Janeba, Zlatko, et al., "Functionalization of Guanosine and 2'-Deoxyguanosine at C6: A Modified Appel Process and $S_NAr$ Displacement of Imidazole," *Nucleosides, Nucleotides & Nucleic Acids*, 23(1&2):137-147 (2004).
Kamaike, Kazuo, et al., "An Efficient Methodfor the Synthesis of [$4^{-15}$N]Cytidine and [$6^{-15}$N]Adenosine Derivatives from Uridine and Inosine," *Tetrahedron Letters*, 36(1):91-94 (1995).
Lin, Xiaoyu, et al., "Mild and Efficient Functionalization at C6 of Purine 2'-Deoxynucleosides and Ribonucleosides," *Organic Letters*, 2(22): 3497-3499 (2000).
Liu, Jiangqiong, et al., "Azoles as Suzuki Cross-Coupling Leaving Groups: Syntheses of 6-Arylpurine 2'-Deoxynucleosides and Nucleosides from 6-(Imidazol-1-yl)- and 6-(1,2,4-Triazol-4-yl)purine Derivatives," *Organic Letters*, 6(19):3421-3423 (2004).
Miles, Robert W., et al., "Nucleic Acid Related Compounds. 86. Nucleophilic Functionalization of Adenine, Adenosine, Tubercidin, and Formycin Derivatives via Elaboration of the Heterocyclic Amino Group into a Readily Displaced 1,2,4-Triazol-4-yl Substituent," *J. Am. Chem. Soc.*, 117(22):5951-5957 (1995).
Miles, Robert W., et al., "Nucleic Acid Related Compounds. 87. Nucleophilic Functionalization of Cytidine and 2'-Deoxycytidine Derivatives via Elaboration of the 4-Amino Group into a readily Displaced 1,2,4-Triazol-4-yl Substituent,," *J. Org. Chem.*, 60(21):7066-7069 (1995).
Pochet, Sylvie, et al., "Synthesis of DNA Fragments Linked to a Solid Support," *Tetrahedron*, 43(15):3481-3490 (1987).

(Continued)

*Primary Examiner*—Patrick T Lewis
(74) *Attorney, Agent, or Firm*—Ryan L. Marshall; Brinks Hofer Gilson & Lione

(57) ABSTRACT

A process for providing regiospecific and highly stereoselective synthesis of 9-β anomeric purine nucleoside analogs is described. The introduction of the sugar moiety on to 6-(azolyl)-substituted purine bases is performed so that highly stereoselective formation of the β anomers of only the 9 position regioisomers of the purine nucleoside analogs (either D or L enantiomers) is obtained. This regiospecific and stereoselective introduction of the sugar moiety allows the synthesis of nucleoside analogs, and in particular 2'-deoxy, 3'-deoxy, 2'-deoxy-2'-halo-arabino and 2',3'-dideoxy-2'-halo-threo purine nucleoside analogs, in high yields without formation of the 7-positional regioisomers. Processes for providing novel 6-(azolyl)purines for the regiospecific and highly stereoselective synthesis of 9-β anomeric purine nucleoside analogs are described. The compounds are drugs or intermediates to drugs.

22 Claims, No Drawings

OTHER PUBLICATIONS

Raić, Silvana, et al., "Acyclic purine nucleoside analogues: computational and NMR studies of conformational behavior," *Journal of Molecular Structure*, 410-411 (1997) 31-33.

Raić, Silvana, et al., "New Acyclic Purine Nucleoside Analogues Containing Exocyclic Pyrrolo Moiety: Synthetic, NMR and X-ray Crystal Structure Studies," *Croatica Chemica Acta*, 69(3):967-986 (1996).

Robins, Morris J., et al., "Syntheses of Puromycin from Adenosine and 7-Deazapuromycin from Tubercidin, and Biological Comparisons of the 7-Aza/Deaza Pair," *J. Org. Chem.*, 66:8204-8210 (2001).

Samano, Vicente, et al., "Efficient Conversion of 6-Aminopurines and Nucleosides into 6-Substituted Analogues via Novel 6-(1,2,4-Triazol-4-yl)purine Derivatives," *J. Am. Chem. Soc.*, 116(20):9331-9332 (1994).

Véliz, Eduardo A., et al., "6-Bromopurine Nucleosides as Reagents for Nucleoside Analogue Synthesis," *J. Org. Chem.*, 66:8592-8598 (2001).

\* cited by examiner

METHODS FOR SELECTIVE N-9 GLYCOSYLATION OF PURINES

TECHNICAL FIELD OF THE INVENTION

The present invention relates to methods for producing purine derivatives that are useful as medicinal agents through N-9 regioselective and N-9 regiospecific glycosylation of 6-(azolyl)purines.

BACKGROUND OF THE INVENTION

Nucleoside derivatives which can be selectively incorporated into viral DNA or RNA to inhibit the replication of viral DNA or RNA, are highly effective agents for treating viral infectious diseases such as herpesvirus, herpes zoster, AIDS, hepatitis, cytomegalovirus and the like. Similarly, such incorporation of nucleoside derivatives into the DNA or RNA of cancer cells can result in tumor cell death and effective treatment of neoplastic diseases. Especially useful are purine derivatives, which have a substituent in the 9-position. These purine derivatives include a large number of significant known compounds having antiviral activity such as acyclovir, ganciclovir, famciclovir, and the like. Also useful for their anticancer activity are purine derivatives such as cladribine (2-CdA), fludarabine, clofarabine, and the like.

Achieving regiospecific and stereoselective glycosylation of purine derivatives at the 9-position is difficult. Glycosylation procedures in which a 2-deoxysugar moiety is coupled with an aglycon invariably provide anomeric mixtures as well as positional isomers, which can result in low yields of the desired nucleoside and often requires troublesome purification protocols. A simplified procedure for N-9 glycosylation that is regiospecific would be highly desirable.

Attempts to enhance N-9 regioselective glycosylation have been made. Gupta et al. (U.S. Patent Application Publication 2004/0039190) describes glycosylation of 6-(acylamido)purines, but notes that the disclosed procedure also produces N-7 glycosylate products. Others have noted that the introduction of larger substituents at C-6 of the purine ring can result in larger ratios of N-9 to N-7 isomer products from simple alkylation reactions (Tetrahedron 1990, 46, 6903). Alarcon et al. (Tetrahedron Lett. 2000, 41, 7211) prepared 2-amino-6-(1,2,4-triazol-4-yl)purine, and reported that alkylation of its sodium salt in DMF with methyl iodide or 1-bromopropane gave the simple N-9 alkyl isomers. Alarcon et al. attributed this selectivity to the introduction of a bulky easily hydrolysable group at C-6 of the purine ring. The use of 6-(acylamido)purines in coupling reactions with sugar derivatives has been performed. Gupta et al. apply potassium salts of 6-(acylamido)purines to prepare 9-glycosyl derivatives of purines that are contaminated with lesser amounts of the 7-glycosyl isomers. Glycosyl coupling with a purine sodium salt in a polar aprotic solvent such as DMF is known to give anomeric mixtures of nucleosides resulting from extensive isomerization of the halo sugar intermediate. Such conditions give stereo- and regioisomeric mixtures as well as extensive sugar decomposition by-products. Gupta et al. use anhydrous THF as a solvent and the strong base potassium hexamethyldisilazide (KHMDS) in toluene to generate potassium salts of 6-(acylamido)purines, followed by addition of the sugar glycosyl chloride derivative. No attempt to enhance the respective solubilities of the 6-(acylamido)purine and sugar derivative was noted.

SUMMARY OF THE INVENTION

The invention provides methods for preparing regiospecific and highly stereoselective synthesis of 9-β anomeric purine nucleosides including 2'-deoxy, 3'-deoxy, 2'-deoxy-2'-halo-arabino and 2',3'-dideoxy-2'-halo-threo purine nucleoside analogs, in high yields without formation of the 7-positional regioisomers.

In one embodiment, the invention provides a method that includes (a) glycosylating a 6-(azolyl)purine at the N-9 position and (b) displacing the 6-(azolyl) group from the glycosylate from step (a) with a nucleophile to yield an N-9 purine nucleoside.

In another embodiment, the invention provides a method that includes (a) introducing an (azolyl) group at the 6 position of a purine, (b) glycosylating the purine product from step (a) at the N-9 position and (c) displacing the 6-(azolyl) group from step (a) with a nucleophile to yield an N-9 purine nucleoside.

The invention also provides a method that includes (a) contacting a 6-(azolyl)-substituted purine of Formula I

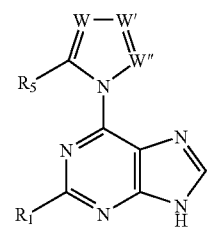

with a glycosylating agent in the presence of a base, where each W, W' and W" is independently selected from —N—, —CH— and $CR_2$, and where $R_1$, $R_2$, and $R_5$ are independently selected from hydrogen, $C_{1-10}$ allyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl, (b) alkylating the appended 6-(azolyl) ring on the 6-substituted purine nucleoside from step (a), (c) contacting the alkylated 6-substituted purine nucleoside from step (b) with ammonia to obtain a nucleoside of Formula III

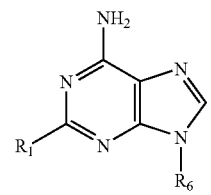

where $R_6$ is a glycosyl group.

In some embodiments, a method of the invention involves a 6-(imidazol-1-yl)purine of Formula XV

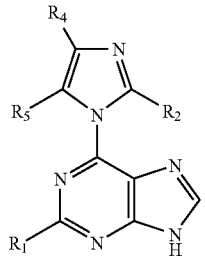

where $R_4$ is selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl.

In some embodiments, a method of the invention involves a 6-(1,2,4-triazol-4-yl)-substituted purine of Formula XXII.

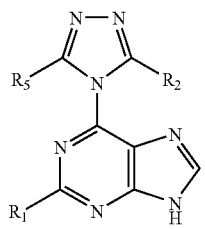

In some embodiments, a method of preparing 2-chloro-2'-deoxyadenosine (2-CdA, cladribine) comprises (a) contacting a compound having Formula XXVIII

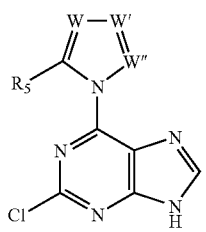

where each W, W' and W'' is independently selected from —N—, —CH— and $CR_2$, where $R_2$ and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl, with a base in a first polar solvent followed by contacting an activated and hydroxyl-protected 2-deoxy-α-D-erythro-pentofuranosyl compound in a second less polar solvent to form a glycosylate product, (b) contacting the glycosylate product from step (a) with ammonia in a third solvent to obtain cladribine.

In some embodiments, a method for preparing 2-chloro-2'-deoxyadenosine (2-CdA, cladribine) comprises (a) contacting a compound having Formula XXVIII

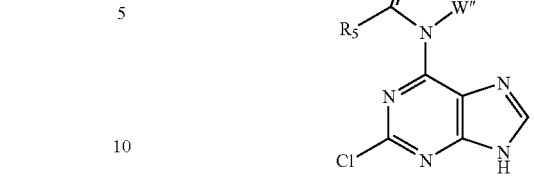

where each W, W' and W'' is independently selected from —N—, —CH— and $CR_2$, and where $R_2$ and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl, with a base in a first polar solvent followed by contacting an activated and hydroxyl-protected 2-deoxy-α-D-erythro-pentofuranosyl compound in a second less polar solvent to form a glycosylate product, (b) alkylating the appended 6-(azolyl) ring on the 6-substituted purine nucleoside from step (a), (c) contacting the alkylated glycosylate product from step (b) with ammonia in a third solvent to obtain cladribine.

In some embodiments, a method of preparing cladribine involves a compound having Formula XXIX.

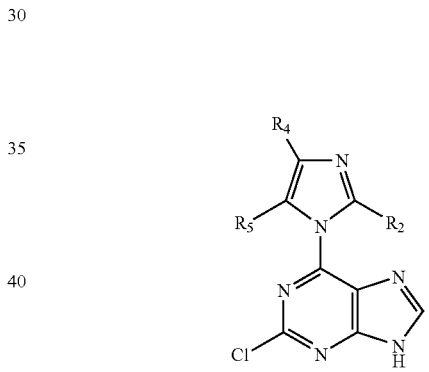

In some embodiments, a method of preparing cladribine involves a compound having Formula XXX.

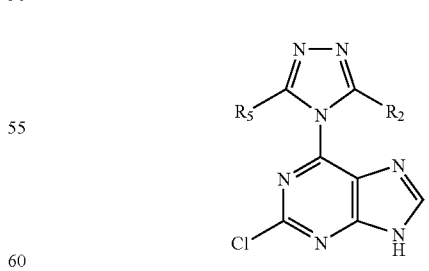

In some embodiments, a method for preparing a 6-(azolyl)-substituted purine includes (a) introducing an azolyl ring at the 6 position of a purine nucleoside and (b) cleaving the glycosidic bond of the nucleoside from step (a) to yield a 6-(azolyl)purine.

In some embodiments, a method for preparing a purine of Formula I

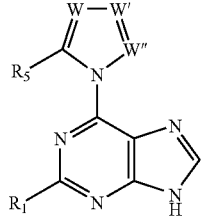

where each W, W' and W" is independently selected from —N—, —CH— and CR$_2$, and where R$_1$, R$_2$, and R$_5$ are independently selected from hydrogen, C$_{1-10}$ alkyl, C$_{1-10}$ alkoxy, C$_{1-10}$ alkylthio, halogen, amino, C$_{1-10}$ alkylamino, di-C$_{1-10}$ alkylamino, C$_{1-10}$ acylamino, aryl, and heteroaryl includes contacting a compound of Formula XXXI:

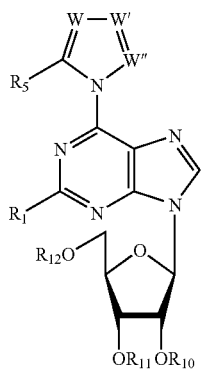

where R$_{10}$, R$_{11}$, and R$_{12}$ are hydroxyl-protecting groups, with a deglycosylation agent.

In some embodiments of the invention, a method for preparing a purine of Formula XV

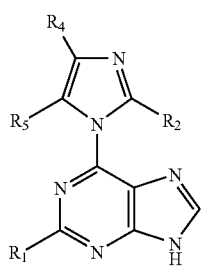

where R$_1$, R$_2$, R$_4$, and R$_5$ are independently selected from hydrogen, C$_{1-10}$ alkyl, C$_{1-10}$ alkoxy, C$_{1-10}$ alkylthio, halogen, amino, C$_{1-10}$ alkylamino, di-C$_{1-10}$ alkylamino, C$_{1-10}$ acylamino, aryl, and heteroaryl, includes a compound of Formula XXXII

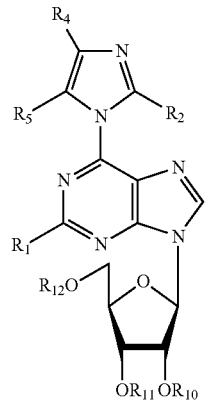

where R$_{10}$, R$_{11}$, and R$_{12}$ are hydroxyl protecting groups, with a deglycosylation agent.

In some embodiments of the invention, a method for preparing a purine of Formula XXII

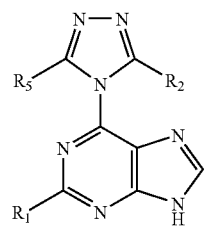

where R$_1$, R$_2$, and R$_5$ are independently selected from hydrogen, C$_{1-10}$ alkyl, C$_{1-10}$ alkoxy, C$_{1-10}$ alkylthio, halogen, amino, C$_{1-10}$ alkylamino, di-C$_{1-10}$ alkylamino, C$_{1-10}$ acylamino, aryl, and heteroaryl, includes contacting a compound of Formula XXXIII

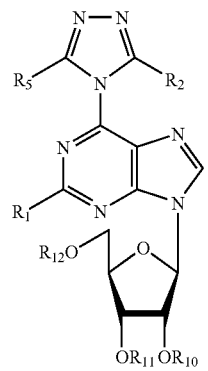

where R$_{10}$, R$_{11}$, and R$_{12}$ are hydroxyl protecting groups, with a deglycosylation agent.

In some embodiments of the invention, a compound of Formula I

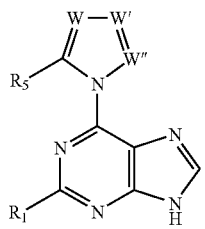

is described where each W, W' and W'' is independently selected from —N—, —CH— and CR$_2$, and where at least one of W, W' and W'' is —N—, R$_1$, R$_2$, and R$_5$ are independently selected from hydrogen, C$_{1-10}$ alkyl, C$_{1-10}$ alkoxy, C$_{1-10}$ alkylthio, halogen, amino, C$_{1-10}$ alkylamino, di-C$_{1-10}$ alkylamino, C$_{1-10}$ acylamino, aryl, and heteroaryl and pharmaceutically acceptable salts of these compounds, provided that (1) when R$_1$ is amino and both W and W' are N, then R$_5$ is not hydrogen, (2) when R$_1$ is hydrogen and W' and W'' are CH, then R$_5$ is not hydrogen, (3) when R$_1$ is hydrogen and R$_5$ is methyl, then W' and W'' are not CH, (4) when R$_1$ and R$_5$ are hydrogen and W' is CCH$_3$, then W'' is not CH, (5) when R$_1$ and R$_5$ are hydrogen and W' is CH, then W'' is not N, (6) when R$_1$ and R$_5$ are hydrogen and W'' is N, then W and W' are not CH, (7) when R$_1$ and R$_5$ are hydrogen and W'' is N, then W is not CCH$_3$, and (8) when R$_1$ and R$_5$ are hydrogen and W'' is N, then W' is not CCH$_3$.

In some embodiments of the invention, a compound of Formula XV

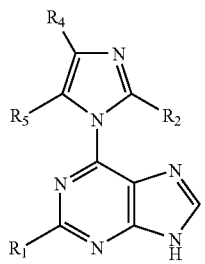

is described where R$_1$, R$_2$, R$_4$, and R$_5$ are independently selected from hydrogen, C$_{1-10}$ alkyl, C$_{1-10}$ alkoxy, C$_{1-10}$ alkylthio, halogen, amino, C$_{1-10}$ alkylamino, di-C$_{1-10}$ alkylamino, C$_{1-10}$ acylamino, aryl, and heteroaryl and pharmaceutically acceptable salts of these compounds, provided that (1) when R$_1$, R$_2$ and R$_4$ are hydrogen, then R$_5$ is not hydrogen, (2) when R$_1$, R$_2$ and R$_5$ are hydrogen, then 4 is not methyl, and (3) when R$_1$, R$_4$ and R$_5$ are hydrogen, then R$_2$ is not methyl.

In some embodiments of the invention, a compound of Formula XXII

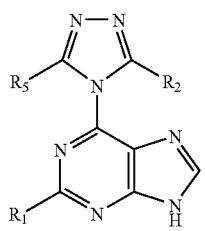

is described where R$_1$, R$_2$, and R$_5$ are independently selected from hydrogen, C$_{1-10}$ alkyl, C$_{1-10}$ alkoxy, C$_{1-10}$ alkylthio, halogen, amino, C$_{1-10}$ alkylamino, di-C$_{1-10}$ alkylamino, C$_{1-10}$ acylamino, aryl, and heteroaryl and pharmaceutically acceptable salts of these compounds, provided that when R$_1$ is amino, then at least one of R$_2$ and R$_5$ is not hydrogen.

In some embodiments of the invention, a compound of Formula XXXVI

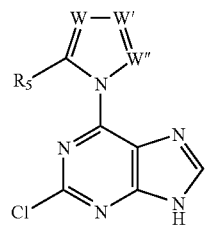

is described where each W, W' and W'' is independently selected from —N—, —CH— and CR$_2$, and where at least one of W, W' and W'' is —N—, and where R$_2$ and R$_5$ are independently selected from hydrogen, C$_{1-10}$ alkyl, C$_{1-10}$ alkoxy, C$_{1-10}$ alkylthio, halogen, amino, C$_{1-10}$ alkylamino, di-C$_{1-10}$ alkylamino, C$_{1-10}$ acylamino, aryl, and heteroaryl and pharmaceutically acceptable salts of these compounds.

DETAILED DESCRIPTION OF THE INVENTION

The term "alkyl" as used herein means aliphatic carbon substituents of the alkane, alkene, and alkyne families, straight-chain or branched-chain, with or without other substituents on the carbon atoms of the chain, and also includes cyclic-"alkyl" substituents of the noted categories.

The term "aglycon" as used herein means the non-sugar component of a glycoside molecule. Hydrolysis of a glycoside can result in the aglycon and the sugar compound.

The term "glycosyl group" as used herein means the structure obtained by removing the hydroxyl group from the hemiacetal function of a protected or unprotected monosaccharide or a lower oligosaccharide.

The term "glycoside" as used herein means the attachment of a glycosyl group to a non-acyl group, particularly N-glycosides. The bond between the glycosyl group and the non-acyl group is called a glycosidic or glycosyl bond.

The term "nucleoside" as used herein refers to a molecule composed of a heterocyclic nitrogenous base, particularly a purine, containing an N-glycosidic linkage with a sugar, particularly a pentose. Nucleosides include both L- and D-nucleoside enantiomers. For brevity, only the structures of the D enantiomers are shown in all drawings; the enantiomeric L structures are the mirror images of the D isomers shown.

The term "ribofuranosyl nucleoside" as used herein refers to a nucleoside or nucleoside analog containing a 2'-hydroxyl group in an L- or D-β-ribofuranosyl configuration.

The term "arabinofuranosyl nucleoside" as used herein refers to a nucleoside or nucleoside analog containing a 2'-hydroxyl group in an L- or D-β-arabinofuranosyl configuration.

The term "nucleophile" as used herein refers to an electron-rich reagent that is an electron pair donor (contains an unshared pair of electrons) and forms a new bond to a carbon atom. Nucleophiles can be anions or neutrally charged. Examples include, but are not limited to, carbanions, oxygen anions, halide anions, sulfur anions, nitrogen anions, nitrogen bases, alcohols, ammonia, water, and thiols.

The term "leaving group" as used herein refers to a weakly basic chemical entity that is released from carbon, and takes the pair of bonding electrons binding it with the carbon atom. Leaving groups can be chemical functional groups that can be displaced from carbon atoms by nucleophilic substitution. Examples include, but are not limited to, halides including chloride, bromide, and iodide, alkylsulfonates, substituted alkylsulfonates, arylsulfonates, substituted arylsulfonates, heterocyclicsulfonates, and trichloroacetimidate groups. Preferred leaving groups include, but are not limited to, chloride, bromide, iodide, p-nitrobenzenesulfonate (nosylate), p-(2,4-dinitroanilino)benzenesulfonate, benzenesulfonate, methylsulfonate (mesylate), p-methylbenzenesulfonate (tosylate), p-bromobenzenesulfonate (brosylate), trifluoromethylsulfonate (triflate), 2,2,2-trifluoroethanesulfonate, imidazolesulfonate, trichloroacetimidate, trifluoroacetate and other acylates, and 2,4,6-trichlorophenoxide.

The synonymous terms "hydroxyl protecting group" and "alcohol-protecting group" as used herein refer to substituents attached to the oxygen of an alcohol group commonly employed to block or protect the alcohol functionality while reacting other functional groups on the compound. Examples of such alcohol-protecting groups include the 2-tetrahydropyranyl group, 2-(bisacetoxyethoxy)methyl group, trityl group, trichloroacetyl group, carbonate-type blocking groups such as benzyloxycarbonyl, trialkylsilyl groups, examples of such being trimethylsilyl, tert-butyldimethylsilyl, tert-butyldiphenylsilyl, phenyldimethylsilyl, triiospropylsilyl and thexyldimethylsilyl, ester groups, examples of such being formyl, $(C_1-C_{10})$ alkanoyl optionally mono-, di- or tri-substituted with $(C_1-C_6)$ alkyl, $(C_1-C_6)$ alkoxy, halo, aryl, aryloxy or haloaryloxy, the aroyl group including optionally mono-, di- or tri-substituted on the ring carbons with halo, $(C_1-C_6)$ alkyl, $(C_1-C_6)$ alkoxy wherein aryl is phenyl, 2-furyl, carbonates, sulfonates, and ethers such as benzyl, p-methoxybenzyl, methoxymethyl, 2-ethoxyethyl group, etc. The choice of alcohol-protecting group employed is not critical so long as the derivatized alcohol group is stable to the conditions of subsequent reaction(s) on other positions of the compound of the formula and can be removed at the desired point without disrupting the remainder of the molecule. Further examples of groups referred to by the above terms are described by J. W. Barton, "Protective Groups In Organic Chemistry", J. G. W. McOmie, Ed., Plenum Press, New York, N.Y., 1973, and T. W. Greene and P. G. M. Wuts, "Protective Groups in Organic Synthesis", Wiley, New York, N.Y., 1999, which are hereby incorporated by reference. The related terms "protected hydroxyl" or "protected alcohol" define a hydroxyl group substituted with a hydroxyl protecting group as discussed above.

The term "transient protection" as used herein refers to the practice of masking one or more sugar hydroxyl groups of a nucleoside with a protecting group, for example through formation of a trimethylsilyl ether, prior to the introduction of a nucleic acid base protecting group, for example an acyl group, followed by the hydrolysis of the protecting group(s) to reveal (unmask) one or more free hydroxyls.

The terms "azole" and "azolyl" as used herein refer to nitrogenous aromatic compounds with (1) a "pyrrole-type" trivalent nitrogen atom, (2) either 1, 2 or 3 "pyridine-type" aromatic trivalent nitrogen(s), (3) a five-membered ring, and (4) aromaticity. A number of azole groups satisfy these criteria including substituted and unsubstituted pyrazoles, substituted and unsubstituted imidazoles, substituted and unsubstituted triazoles (including the 1,2,3- and 1,2,4-triazoles) and substituted and unsubstituted tetrazoles.

The term "acyl group" as used herein refers to a chemical entity comprising the general formula R—C(O)— where R represents any aliphatic, alicyclic, or aromatic group and C(O) represents a carbonyl group.

The term "acylation" as used herein refers to any process whereby an acid, or an acid derivative such as an acid halide or an acid anhydride is used to convert a hydroxyl group into an ester, or an amine into an amide.

The terms "halogen" or "halo" as used herein refer to fluorine, chlorine, bromine and iodine, and the term "halide" refers to fluoride, chloride, bromide and iodide.

The term "nitrogen protecting group," as used herein, refers to groups known in the art that are readily introduced on to and removed from a nitrogen atom. Examples of nitrogen protecting groups include acetyl (Ac), trifluoroacetyl, Boc, Cbz, benzoyl (Bz), trityl and benzyl (Bn). See also T. W. Greene and P. G. M. Wuts, "Protective Groups in Organic Synthesis", Wiley, New York, N.Y., 1999 and related publications.

The term "torsion angle" as used herein refers to the dihedral angle between the plane containing atoms A, B, C and the plane containing B, C, D in a chain of atoms A-B-C-D. Stereochemical arrangements corresponding to torsion angles between 0° and ±90° are called syn (s), those corresponding to torsion angles between ±90° and 180° anti (a). Similarly, arrangements corresponding to torsion angles between 30° and 150° or between −30° and −150° are called clinal (c) and those between 0° and 30° or 150° and 180° are called periplanar (ap). The two types of terms can be combined so as to define four ranges of torsion angle; 0° to 30° synperiplanar (sp); 30° to 90° and −30° to −90° synclinal (sc); −90° to 150° and −90° to −150° anticlinal (ac); ±150° to 180° antiperiplanar (ap).

The compounds described herein and used or made in the methods described herein can contain one or more asymmetric carbon atoms (chirality centers), so that the compounds can exist in different stereoisomeric forms. These compounds can be, for example, racemic mixtures, optically active non-racemic mixtures or diastereomers. In these situations, the single enantiomers, i.e., optically pure forms, can be obtained by asymmetric synthesis or by resolution of racemic mixtures. Resolution of racemic mixtures can be accomplished, for example, by conventional methods such as crystallization in the presence of a resolving agent, chromatography, using, for example a chiral HPLC column, or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

In one aspect, a novel method for preparing N-9 purine nucleosides is provided. In one embodiment, a method for preparing an N-9 purine nucleoside, comprises the steps of:

(a) glycosylating a 6-(azolyl)purine at the N-9 position; and, (b) displacing the azolyl group from the glycosylate in step (a) with a nucleophile to yield an N-9 purine nucleoside.

In some embodiments, the method results in highly regioselective glycosylation, and in some embodiments, the method results in regiospecific glycosylation.

In some embodiments, the method results in a substantially pure regioisomer, and in some embodiments, the method results in a substantially pure regio- and stereoisomer.

In some embodiments, the 6-azolyl substituent is selected from the group consisting of unsubstituted imidazole and unsubstituted triazole. In some embodiments, the 6-azolyl substituent is selected from the group consisting of substituted imidazoles and substituted triazoles. In some embodiments, the 6-azolyl substituent is selected from the group consisting of unsubstituted imidazole and substituted imidazoles. In some embodiments, the 6-azolyl substituent is selected from the group consisting of unsubstituted triazole and substituted triazoles. In some embodiments, the 6-azolyl substituent is selected from the group consisting of 1,2,3- and 1,2,4-triazoles and substituted 1,2,3- and 1,2,4-triazoles.

In some embodiments, the nucleophile in step (b) is a nitrogen-containing nucleophile that is converted into an amino substituent by a subsequent transformation (e.g., azide followed by reduction, benzylamine followed by hydrogenolysis, etc.).

In one embodiment, the nucleophile in step (b) is ammonia.

In other embodiments, the nucleophile in step (b) is an oxygen- or sulfur-nucleophile.

In another aspect, a method for preparing an N-9 purine nucleoside, comprises the steps of:

(a) introducing an azolyl group at the 6 position of a purine;
(b) glycosylating the 6-(azolyl)purine product from step (a) at the N-9 position; and,
(c) displacing the 6-azolyl group with a nucleophile to yield an N-9 purine nucleoside.

In some embodiments, the method results in highly regioselective glycosylation and in some embodiments, the method results in regiospecific glycosylation.

In some embodiments, the method results in a substantially pure regioisomer, and in some embodiments, the method results in a substantially pure regio- and stereoisomer.

In some embodiments, the 6-azolyl substituent is selected from the group consisting of unsubstituted imidazole and unsubstituted triazole. In some embodiments, the 6-azolyl substituent is selected from the group consisting of substituted imidazoles and substituted triazoles. In some embodiments, the 6-azolyl substituent is selected from the group consisting of unsubstituted imidazole and substituted imidazoles. In some embodiments, the 6-azolyl substituent is selected from the group consisting of unsubstituted triazole and substituted triazoles. In some embodiments, the 6-azolyl substituent is selected from the group consisting of 1,2,3- and 1,2,4-triazoles and substituted 1,2,3- and 1,2,4-triazoles.

In some embodiments, the nucleophile in step (b) is a nitrogen-containing nucleophile that is converted into an amino substituent by a subsequent transformation (e.g., azide followed by reduction, benzylamine followed by hydrogenolysis, etc.).

In one embodiment, the nucleophile in step (c) is ammonia.

In other embodiments, the nucleophile in step (b) is an oxygen- or sulfur-nucleophile.

In some embodiments an azolyl substituent is introduced at the 6 position of the purine by contacting the purine with an azole under nucleophilic displacement conditions. Alternatively, the azole can be formed at the 6 position on the purine by cyclization of a 6-aminopurine with an azine or substituted hydrazine.

Suitable agents for introducing an azolyl group on to a 6-substituted purine with a leaving group at the 6 position include substituted and unsubstituted imidazoles and substituted and unsubstituted triazoles. Nucleophilic displacement reactions can transpire in polar unreactive solvents such as dimethylformamide or acetonitrile at about 15° to about 100° C.

Suitable agents for cyclization reactions to introduce an azolyl group on to a 6-aminopurine include, for example, 1,2-bis[(dimethylamino)methylene]hydrazine, 1,2-diformylhydrazine, and other 1,2-diacylhydrazines. Cyclization reactions can transpire in polar unreactive solvents such as dimethylformamide at between about 35° to about 200° C.

Suitable agents for adding an azolyl group at the 6 position when the purine has a carbonyl group at the 6 position (such as guanine and hypoxanthine bases) include substituted and unsubstituted imidazoles, substituted and unsubstituted triazoles. Such reactions can be performed using triphenyl phosphine ($Ph_3P$), iodine ($I_2$), and an aprotic base such as diisopropylethylamine ($EtN(i-Pr)_2$) in an aprotic solvent such as toluene at elevated temperatures from about 35° to about 120°.

In some embodiments, the glycosylation step is performed by contacting a glycosylating agent in an unreactive solvent with an anionic 6-(azolyl)purine salt, in which the azolyl ring at the 6-position is substantially coplanar with or periplanar with the purine ring.

Suitable glycosylation agents for glycosylating a 6-(azolyl)purine include, but are not limited to, pentofuranoses, 2-deoxypentofuranoses, 3-deoxypentofuranoses, 2,3-dideoxypentofuranoses, substituted pentofuranoses, substituted 2-deoxypentofuranoses, substituted 3-deoxypentofuranoses and substituted 2,3-dideoxypentofuranoses, and analogs of all of the above classes of carbohydrate derivatives with a sulfur atom in place of the furanosyl ring oxygen atom, all with protected alcohol (OH) groups. Preferably, the activated sugar is selected from a group consisting of activated and O-protected sugars including, but not limited to, 2,3,5-tri-O-acetyl-β-D- or L-ribofuranosyl chloride, 2,3,5-tri-O-benzoyl-β-D- or L-ribofuranosyl bromide, 2-deoxy-3,5-di-O-p-toluoyl-α-D- or L-erythro-pentofuranosyl chloride, 3-deoxy-2,5-di-O-benzoyl-β-D- or L-erythropentofuranosyl chloride, 2-deoxy-2-fluoro-3,5-di-O-benzoyl-α-D- or L-arabinofuranosyl bromide, 2,3-dideoxy-2-fluoro-5-O-p-toluoyl-α-D- or L-glycero-pentofuranosyl chloride (also called 2,3-dideoxy-2-fluoro-5-O-p-toluoyl-α-D- or L-arabinofuranosyl chloride), 2-deoxy-2,2-difluoro-3,5-di-O-benzoyl-β-D- or L-erythro-pentofuranosyl triflate and 2,3,5-tri-O-benzyl-α-D- or L-arabinofuranosyl bromide, and their analogs with a sulfur atom in place of the furanosyl ring oxygen atom. In these embodiments, chloride and bromide are leaving groups. Other leaving groups may be substituted for the chloride or bromide leavings groups including, but not limited to, fluoride, iodide, triflate, mesylate, tosylate, trichloroacetimidate, acetate, benzoate, and other acylates, etc. Other hydroxyl protecting groups, which are familiar to those skilled in the art, may be substituted for the indicated acetyl, benzoyl, p-toluoyl, etc. groups.

Suitable glycosylating agents may also be represented by Formula XXXVIII

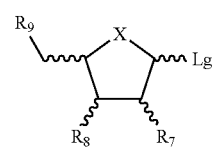

in which Lg is a leaving group; $R_7$, $R_8$ and $R_9$ are each independently selected from hydrogen, protected hydroxyl, halogen including fluoro, chloro, bromo and iodo, alkyl ($C_1$-$C_6$), alkoxyl ($C_1$-$C_6$), protected nitrogen; and X is oxygen, sulfur or a nitrogen atom with a bonded hydrogen atom, an alkyl ($C_1$-$C_6$) or an acyl group.

Glycosylations can be carried out using glycosylating agents with transiently protected hydroxyl groups.

Glycosylations can be performed in solutions of mixed solvents with a minimum amount of a more polar (higher dielectric constant) unreactive solvent such as acetonitrile or dimethylformamide to increase the solubility of the anionic 6-(azolyl)purine salt, and a less polar (lower dielectric constant) unreactive solvent such as chloroform, dichloromethane, tetrahydrofuran, or toluene. The protected and activated sugar derivative can be soluble in the less polar solvent and the low polarity (lower dielectric constant) of that solvent strongly retards ionization of the glycosyl-leaving group bond thus minimizing (or eliminating) anomerization of the activated sugar derivative and maximizing formation of the desired nucleoside diastereoisomer.

Alternatively, glysosylations may be performed in a single solvent. Glycosylations may also be performed in three or more solvents to fine-tune the polarity (average dielectric constant) and preferential solvation characteristics of the combination. The solvents of single and multiple solvent combinations can be anhydrous.

Glycosylations can transpire with a metal salt of a 6-(azolyl)purine, initially formed in situ by treatment of the 6-(azolyl)purine with a hydride base such as sodium hydride or potassium hydride, a strong base such as sodium hexamethyldisilazide or potassium hexamethyldisilazide, or alkaline metal carbonates such as sodium carbonate and potassium carbonate. Glycosylations carried out in polar solvent systems can solubilize partially or fully the resultant metal salt of a 6-(azolyl)purine.

Optionally, strong bases with both organic cation and anion components may be used to enhance the solubility of the resulting purine salt in non-polar solvents. When strong bases with organic cation and anion components are used, glycosylations with an anionic 6-(azolyl)purine salt may be carried out in a single solvent.

Optionally, catalysts such as sodium iodide can be included. The glycosylations can be conducted at temperatures from about 0° to about 50° C. Glycosylations may proceed very slowly at temperatures below 0° C. Glycosylation may be carried out at a temperature that is about room temperature (~25° C.).

In some embodiments, the appended 6-(azolyl) ring and the purine ring have a dihedral angle of between about 0° and about 3°. In other embodiments, the appended 6-(azolyl) ring and the purine ring have a dihedral angle of between about 0° and about 5°. In other embodiments, the appended 6-(azolyl) ring and the purine ring have a dihedral angle of between about 0° and about 10°. In still other embodiments, the appended 6-(azolyl) ring and the purine ring have a dihedral angle of between about 0° and about 15°. In other embodiments, the appended 6-(azolyl) ring and the purine ring have a dihedral angle of between about 0° and about 20°. In other embodiments, the appended 6-(azolyl) ring and the purine ring have a dihedral angle of between about 0° and about 25°. In still other embodiments, the appended 6-(azolyl) ring and the purine ring have a dihedral angle of between about 0° and about 30°. In other embodiments, the appended 6-(azolyl) ring and the purine ring have a dihedral angle of between about 0° and about 35°. In still other embodiments, the appended 6-(azolyl) ring and the purine ring have a dihedral angle of between about 0° and about 45°. In some embodiments, the appended 6-(azolyl) ring and the purine ring have a dihedral angle of between about 0° and about 90°.

When regiospecificity is unnecessary (or undesired), highly regioselective glycosylations may nevertheless be obtained when the dihedral angle between the appended 6-(azolyl) ring and the purine ring is between about 0° and about 90° or between about 0° and about 45°.

In some embodiments following glycosylation, step (c) may be performed by activation of the appended 6-(azolyl) ring using a reactive alkylating agent followed by nucleophilic displacement of the alkylated 6-(azolyl) group. In some embodiments, concomitant displacement of the 6-(azolyl) group and any O-protection groups can occur by direct ammonolysis at the 6-position.

Feasible reactive alkylating agents include allylic alkyl halides as well as benzyl halides, α-alkoxyalkyl halides, and the like. The alkylated 6-(azolyl)-substituted nucleoside undergoes ammonolysis by heating a solution of the nucleoside in a solvent containing ammonia at an elevated temperature relative to room temperature and at as much as about 100° C., until the reaction is complete, usually for a period of from about 5 to about 12 hours. In one embodiment, the solvent containing ammonia is methanol, commonly referred to as methanolic ammonia.

In some embodiments following glycosylation, displacement of the appended 6-(azolyl) ring by a hydroxide nucleophile gives the corresponding 6-oxopurine compound. In some embodiments, concomitant displacement of the 6-(azolyl) group and any O-protection groups occurs by base-promoted hydrolysis at the 6-position.

In some embodiments following glycosylation, displacement of the appended 6-(azolyl) ring by a nitrogen-, oxygen- or sulfur-based nucleophile gives the corresponding 6-(substituted-amino)-, 6-(disubstituted-amino)-, 6-(substituted-oxy)- or 6-(substituted-sulfanyl)purine compound in which the substituents on nitrogen, oxygen, or sulfur are chosen from groups including, but not limited to, hydrogen, alkyl ($C_1$-$C_6$), aryl, heteroaryl and arylalkyl. In some embodiments, concomitant displacement of the 6-(azolyl) group and any O-protection groups occurs.

The N-9 regiospecific glycosylation methods provide efficient access to 9-β-D- or L-purine nucleosides, including the adenosines, guanosines, inosines and substituted derivatives thereof, and deoxynucleosides including the deoxyadenosines, deoxyguanosines, deoxyinosines and substituted derivatives thereof. Specific nucleosides and deoxynucleosides include, but are not limited to, the 2'-deoxyadenosines, 2'-deoxy-α- or β-2'-halogenated-deoxyadenosines, 3'-deoxyadenosines, 2',3'-dideoxyadenosines, 2'-deoxy-2'-β-F-adenosines (such as 2-chloro-2'-deoxy-2'-F-araA, clofarabine), 2',3'-dideoxy-2'-β-F-adenosines, adenine arabinosides such as adenine arabinoside (araA) and 2-F-araA (fludarabine) and the like.

In one embodiment, a method of regiospecific N-9 glycosylation of purines comprises contacting a 6-(azolyl)-substituted purine of Formula I

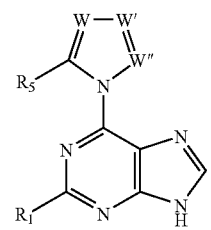

with a base in a more polar solvent, and treating the resulting anionic salt with a glycosylating agent of the formula R₆-Lg wherein each W, W' and W" is independently selected from —N—, —CH— and —CR₂—, and where at least one of W, W' and W" is —N—, and where R₁, R₂, and R₅ are independently selected from hydrogen, C₁₋₁₀ alkyl, C₁₋₁₀ alkoxy, C₁₋₁₀ alkylthio, halogen, amino, C₁₋₁₀ alkylamino, di-C₁₋₁₀ alkylamino, C₁₋₁₀ acylamino, aryl, and heteroaryl, and where R₆ is a glycosyl group, and Lg is a leaving group. The method may be followed by allylation of the appended 6-(azolyl) ring to obtain an activated 6-(azolium) salt of Formula II

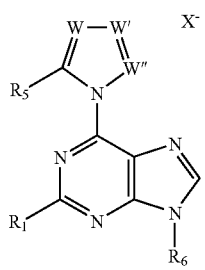

where W, W', and W" are independently selected from —N—, —NR₁₃—, —CH— and —CR₂—, and where one of W, W', and W" is —NR₁₃— and R₁₃ is alkyl or alkylaryl, and where X is a counter anion. The activated nucleoside may be subjected to ammonolysis to obtain nucleosides of Formula III.

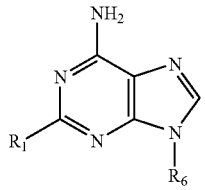

In one such process, 9-β-D- or L-purine 2'-deoxynucleosides, including the deoxyadenosines, are prepared by glycosylating an anionic 6-(azolyl)purine salt derived from a purine having the Formula I

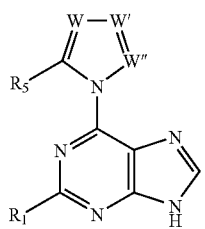

with 2-deoxy-3,5-di-O-p-toluoyl-α-D- or L-erythro-pentofuranosyl chloride. The resulting compound of Formula IV

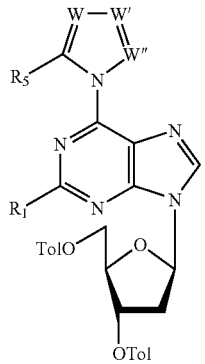

can be optionally alkylated to activate the appended 6-(azolyl) ring followed by ammonolysis at C-6 and the alcohol protecting groups resulting in formation of the 2'-deoxynucleosides of Formula V.

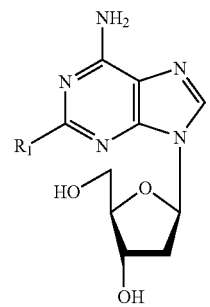

Where the glycosylating agent is 3-deoxy-2,5-di-O-benzoyl-β-D- or L-erythro-pentofuranosyl chloride, glycosylation results in the compound with Formula VI.

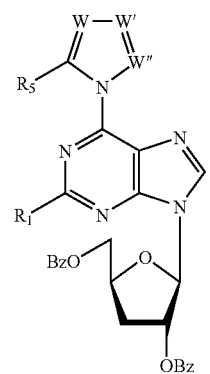

The compound of Formula VI can be optionally alkylated to activate the appended 6-(azolyl) ring followed by ammonolysis at C-6 and the alcohol protecting groups resulting in formation of the 3'-deoxynucleosides of Formula VII.

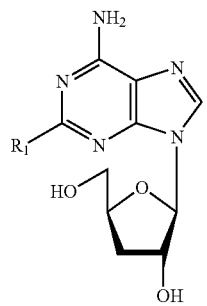

Where the glycosylating agent is 3,5-di-O-benzoyl-2-deoxy-2-fluoro-α-D- or L-arabinofuranosyl bromide, glycosylation results in formation of the compound with Formula VIII.

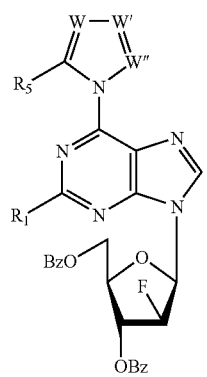

The compound of Formula VIII can be optionally alkylated to activate the appended 6-(azolyl) ring followed by ammonolysis at C-6 and the alcohol protecting groups resulting in formation of the 2'-deoxy-2'-fluoro arabino nucleosides of Formula IX.

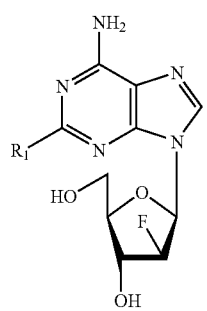

Where the glycosylating agent is 2,3-dideoxy-2-fluoro-5-O-p-toluoyl-α-D- or L-threo-pentofuranosyl chloride, glycosylation results in formation of the compound with Formula X.

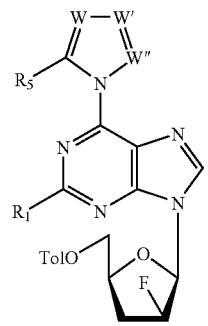

The compound of Formula X can be optionally alkylated to activate the appended 6-(azolyl) ring followed by ammonolysis at C-6 and the alcohol protecting groups resulting in formation of the 2',3'-dideoxy-2'-fluoro threo nucleosides of Formula XI.

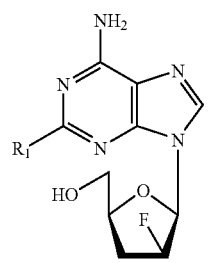

Where the glycosylating agent is 2,3,5-tri-O-benzyl-α-D- or L-arabinofuranosyl bromide, glycosylation results in formation of the compound with Formula XII.

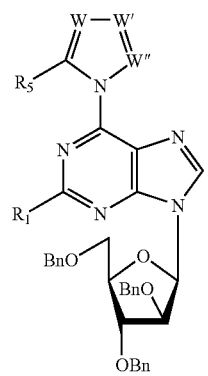

The compound of Formula XII can be optionally alkylated to activate the appended 6-(azolyl) ring followed by ammonolysis at C-6 and removal of the alcohol protecting groups resulting in formation of the nucleoside of Formula XIII.

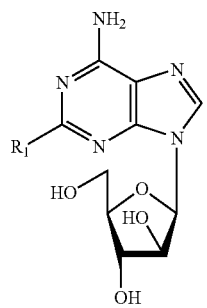

In some embodiments W" is CR$_2$ and has Formula XIV.

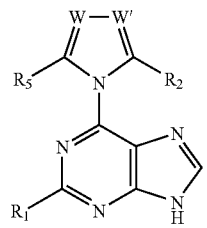

The 2-chloro-2'-deoxyadenosine (cladribine) and 2'-deoxyadenosine products from the aforementioned methods are useful cytotoxic agents and deoxynucleosides useful for the production of 2'-deoxyadenosine analogs (Cancer Res. 1982, 42, 3911). 3'-Deoxyadenosine (cordycepin) is a nucleoside antibiotic having antitumor activity (Suhadolnik, R. J. Nucleoside Antibiotics: New York, Wiley-Interscience). 2-Chloro-3'-deoxyadenosine is a direct analog of cladribine (a useful cytotoxic agent). 2'-F-2'-deoxy-araA is an analog of 2-chloro-2'-F-2'-deoxy-araA (clofarabine, a cytotoxic agent against different human cell lines; murine leukemia L 1210 and P388 leukemia in mice; J. Med. Chem. 1992, 35, 397). 2-Chloro-2'-F-2',3'-dideoxy-araA is an analog of 2'-F-2',3'-dideoxy-araA (an anti-HIV agent, J. Med. Chem. 1990, 33, 978). 2-Fluoro-araA (fludarabine) is the precursor for the synthesis of fludarabine phosphate, an FDA approved product for the treatment of refractory chronic lymphocytic leukemia.

In another embodiment, a method of regiospecific N-9 glycosylation of purines comprises contacting an anionic 6-(imidazol-1-yl)purine salt derived from a 6-(imidazol-1-yl)-substituted purine of Formula XV

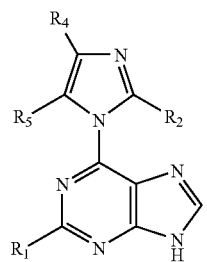

with a glycosylating agent of the Formula R$_6$-Lg. The method may be followed by allylation of the appended 6-(imidazol-1-yl) ring to obtain an activated 6-(3-alkylimidazolium-1-yl) purine nucleoside of Formula XVI

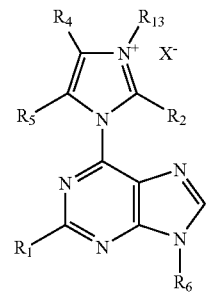

and ammonolysis to obtain nucleosides of Formula III

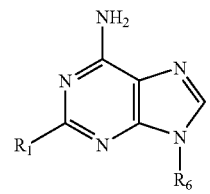

wherein R$_1$, R$_2$, R$_4$, R$_5$ are independently selected from hydrogen, C$_{1-10}$ alkyl, C$_{1-10}$ alkoxy, C$_{1-10}$ alkylthio, halogen, amino, C$_{1-10}$ alkylamino, di-C$_{1-10}$ alkylamino, C$_{1-10}$ acylamino, aryl, and heteroaryl, R$_6$ is a glycosyl group and Lg is a leaving group, R$_{13}$ is alkyl or alkylaryl, and X is a counter anion.

In one such process, 9-β-D- or L-purine 2'-deoxynucleosides, including the deoxyadenosines, are prepared by glycosylating an anionic 6-(azolyl)purine salt derived from a purine having the Formula XV

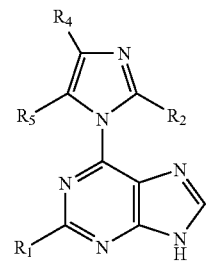

with 2-deoxy-3,5-di-O-p-toluoyl-α-D- or L-erythro-pentofuranosyl chloride. The resulting compound of Formula XVII

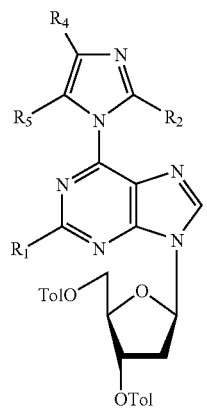

can be optionally alkylated to activate the appended 6-(azolyl) ring followed by ammonolysis at C-6 and the alcohol protecting groups resulting in formation of the 2'-deoxynucleosides of Formula V.

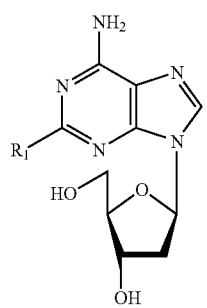

Where the glycosylating agent is 3-deoxy-2,5-di-O-benzoyl-α-D- or L-erythro-pentofuranosyl chloride, glycosylation results in the compound with Formula XVIII.

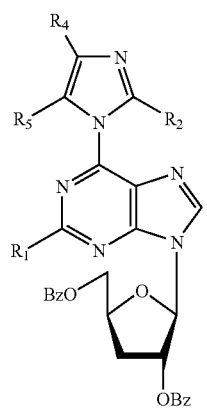

The compound of Formula XVIII can be optionally alkylated to activate the appended 6-(azolyl) ring followed by ammonolysis at C-6 and the alcohol protecting groups resulting in formation of the 3'-deoxynucleosides of Formula VII.

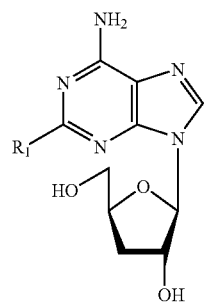

Where the glycosylating agent is 3,5-di-O-benzoyl-2-deoxy-2-fluoro-α-D- or L-arabinofaranosyl bromide, glycosylation results in formation of the compound with Formula XIX.

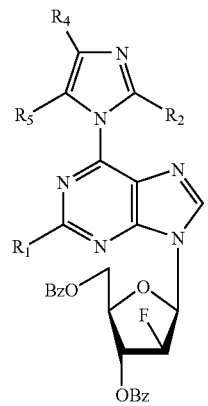

The compound of Formula XIX can be optionally alkylated to activate the appended 6-(azolyl) ring followed by ammonolysis at C-6 and the alcohol protecting groups resulting in formation of the 2'-deoxy-2'-fluoro arabino nucleosides of Formula IX.

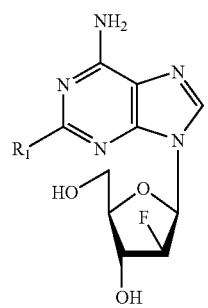

Where the glycosylating agent is 2,3-dideoxy-2-fluoro-5-O-p-toluoyl-α-D- or L-threo-pentofuranosyl chloride, glycosylation results in formation of the compound with Formula XX.

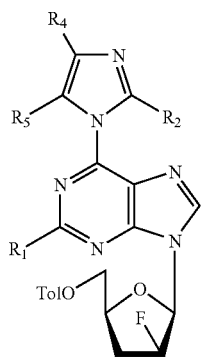

The compound of Formula XX can be optionally alkylated to activate the appended 6-(azolyl) ring followed by ammonolysis at C-6 and the alcohol protecting groups resulting in formation of the 2',3'-dideoxy-2'-fluoro threo nucleosides of Formula XI.

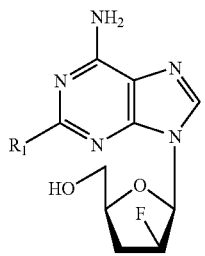

Where the glycosylating agent is 2,3,5-tri-O-benzyl-α-D- or L-arabinofuranosyl bromide, glycosylation results in formation of the compound with Formula XXI.

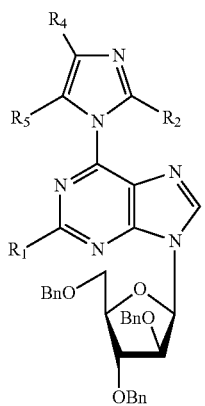

The compound of Formula XXI can be optionally alkylated to activate the appended 6-(azolyl) ring followed by ammonolysis at C-6 and removal of the alcohol protecting groups resulting in formation of the nucleoside of Formula XIII.

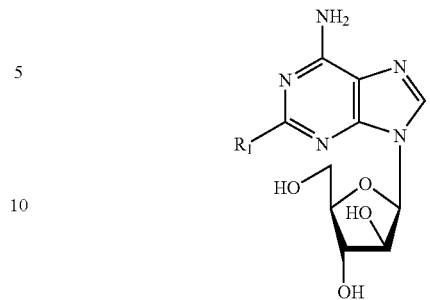

In some embodiments, the sodium salts of the 2-chloro-6-(imidazol-1-yl)purines can be coupled with 2-deoxy-3,5-di-O-(p-toluoyl)-α-D-erythro-pentofuranosyl chloride according to Scheme (1). In some embodiments, the glycosylation is carried out in binary solvent mixtures with the more polar (higher dielectric constant) solvent used to solubilize the purine salt and the non-polar solvent (low dielectric constant) used to dissolve the sugar derivative and minimize anomerization of the glycosyl halide. In other embodiments, the glycosylation is carried out in a single solvent. Various embodiments are given in Table 1.

TABLE 1

Scheme 1

| $R_2$, $R_4$, $R_5$ | 1-β:1-α | % Yield |
|---|---|---|
| H, H, H | 1.85:1 | 71 |
| $CH_2CH_2CH_3$ (propyl), H, H | 1:0 | 83-95 |
| $CH(CH_3)_2$ (isopropyl), H, H | 98:2-1:0 | 100 |
| $CH_2CH_2CH_2CH_3$ (butyl), H, H | 96:4-97:3 | 86 |
| $CH_2CH_2CH_2CH_2CH_3$ (pentyl), H, H | 1:0 | 100 |
| $CH_2CHPhCH_3$ (2-phenylpropyl), H, H | 1:0 | 99 |

TABLE 1-continued

Scheme 1

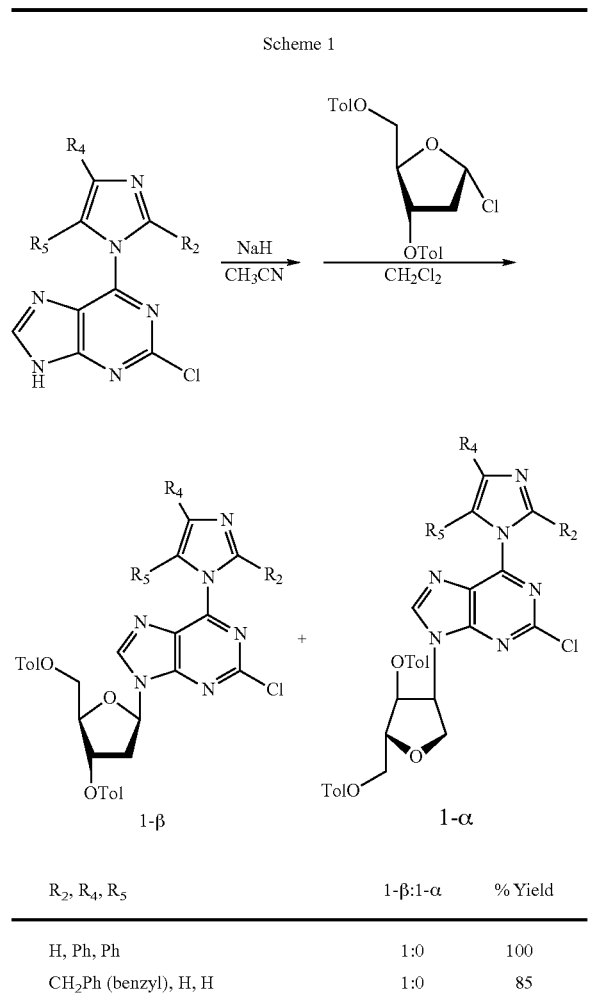

| $R_2$, $R_4$, $R_5$ | 1-β:1-α | % Yield |
|---|---|---|
| H, Ph, Ph | 1:0 | 100 |
| CH₂Ph (benzyl), H, H | 1:0 | 85 |

The β anomers (1-β) from Scheme 1 can be alkylated with benzyl iodide to activate the 6-(imidazol-1-yl) groups followed by ammonolysis at C-6 and the alcohol protecting groups resulting in formation of the cladribine product according to Scheme 2.

Scheme 2

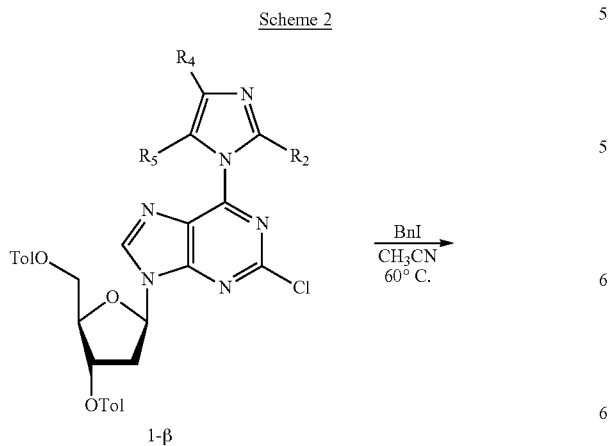

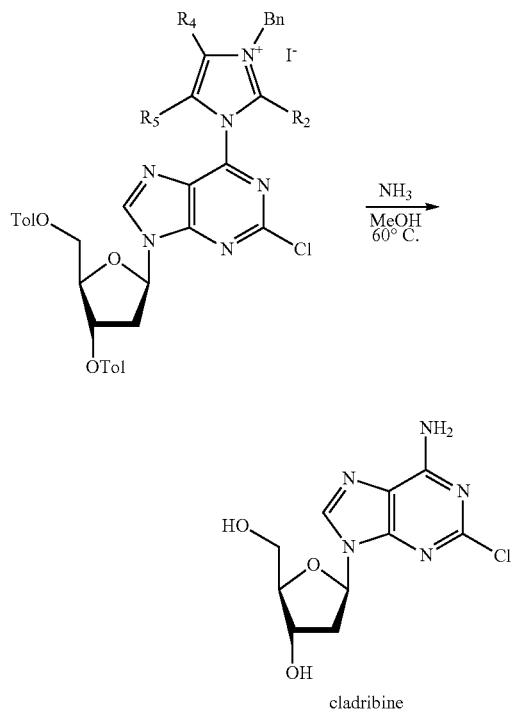

Benzylation of sterically hindered 6-(imidazol-1-yl)purines can result in mixtures of benzylated and nonbenzylated products such as when benzylating 2-chloro-9-[2-deoxy-3,5-di-O-p-toluoyl)-β-D-erythro-pentofuranosyl]-6-(4,5-diphenylimidazol-1-yl)purine, 2-chloro-9-[2-deoxy-3,5-di-O-(p-toluoyl)-β-D-erythro-pentofuranosyl]-6-(2-isopropylimidazol-1-yl)purine. Partial decomposition can also result with 6-(2-benzylimidazol-1-yl)-2-chloro-9-[2-deoxy-3,5-di-O-p-toluoyl)-β-D-erythro-pentofuranosyl]purine.

In another embodiment, a method of regiospecific N-9 glycosylation of purines comprises contacting an anionic 6-(1,2,4-triazol-4-yl)purine salt derived from a 6-(1,2,4-triazol-4-yl)-substituted purine of the Formula XXII with a glycosylating agent of the Formula $R_6$-Lg. The method may be followed by ammonolysis to obtain nucleosides of Formula III

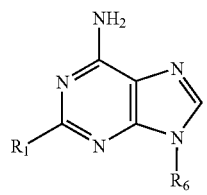

wherein $R_1$, $R_2$, and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl, $R_6$ is a glycosyl group and $Lg$, is a leaving group.

In one such process, 9-β-D- or L-purine 2'-deoxynucleosides, including the deoxyadenosines, are prepared by glycosylating an anionic 6-(1,2,4-triazol-4-yl)purine salt derived from 6-(1,2,4-triazol-4-yl)purine having the Formula XXII

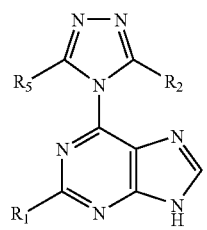

with 2-deoxy-3,5-di-O-p-toluoyl-α-D- or L-erythro-pentofuranosyl chloride. The resulting compound of Formula XXIII

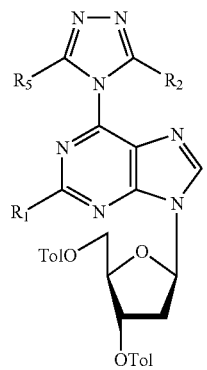

can be subjected to ammonolysis at C-6 and the alcohol protecting groups resulting in formation of the 2'-deoxynucleosides of Formula V.

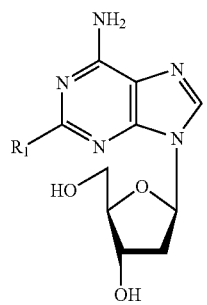

Where the glycosylating agent is 3-deoxy-2,5-di-O-benzoyl-β-D- or L-erythro-pentofuranosyl chloride, glycosylation results in the compound with Formula XXIV.

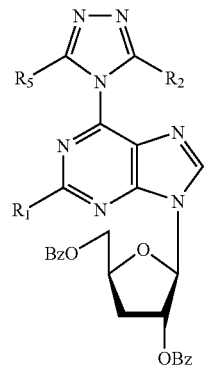

The compound of Formula XXIV can be optionally alkylated to activate the appended 6-(azolyl) ring followed by ammonolysis at C-6 and the alcohol protecting groups resulting in formation of the 3'-deoxynucleosides of Formula VII.

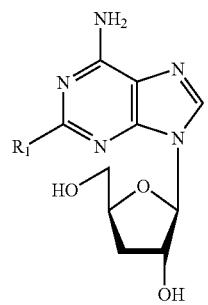

Where the glycosylating agent is 3,5-di-O-benzoyl-2-deoxy-2-fluoro-α-D- or L-arabinofuranosyl bromide, glycosylation results in formation of the compound with Formula XXV.

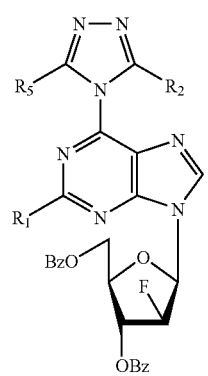

The compound of Formula XXV can be optionally alkylated to activate the appended 6-(azolyl) ring followed by ammonolysis at C-6 and the alcohol protecting groups resulting in formation of the 2'-deoxy-2'-fluoro arabino nucleosides of Formula IX.

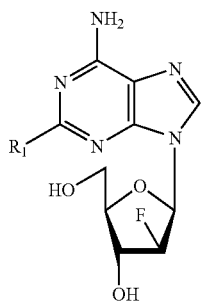

Where the glycosylating agent is 2,3-dideoxy-2-fluoro-5-O-p-toluoyl-α-D- or L-threo-pentofuranosyl chloride, glycosylation results in formation of the compound with Formula XXVI.

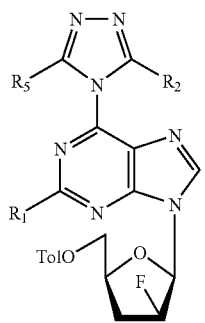

The compound of Formula XXVI can be subjected to ammonolysis at C-6 and the alcohol protecting groups resulting in formation of the 2',3'-dideoxy-2'-fluoro threo nucleosides of Formula XI.

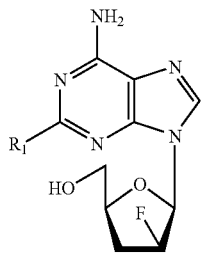

Where the glycosylating agent is 2,3,5-tri-O-benzyl-α-D- or L-arabinofuranosyl bromide, glycosylation results in formation of the compound with Formula XXVII.

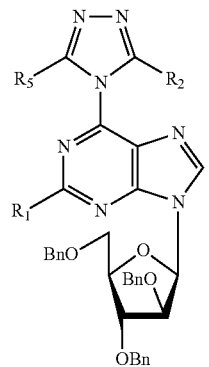

The compound of Formula XXVII can be subjected to ammonolysis at C-6 and removal of the alcohol protecting groups resulting in formation of the nucleoside of Formula XIII.

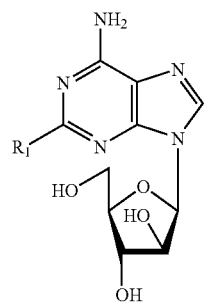

In the embodiments with 6-(imidazol-1-yl)- and 6-(1,2,4-triazol-4-yl)-substituted purines, either of $R_2$ and $R_5$ may be substituted with $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl to enhance solubility of the 6-(azolyl)-substituted purines.

In one embodiment, a method for the preparation of cladribine (2-CdA) comprises:

(a) contacting a compound having Formula XXVIII:

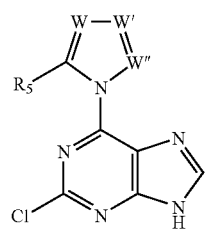

where each W, W' and W" is independently selected from —N—, —CH— and $CR_2$, each of $R_2$ and $R_5$ is independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl, with a base in a first polar solvent followed by contacting an activated and hydroxyl-protected 2-deoxy-α-D-erythro-pentofuranosyl compound in a second less polar solvent to form a nucleoside product, (b) alkylating the appended 6-(azolyl) ring of the nucleoside product from step (a) for activation for nucleophilic displacement at C-6 of the purine ring, (c) contacting the alkylated 6-(azolium) salt from step (b) with ammonia in a third solvent to obtain 2-CdA.

In another embodiment, a method for the preparation of cladribine (2-CdA) comprises:

(a) contacting a compound having Formula XXVIII:

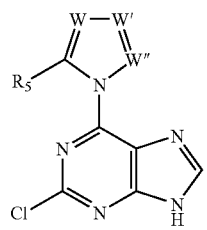

where each W, W' and W" is independently —N—, —CH— or CR$_2$, each of R$_2$ and R$_5$ is independently selected from hydrogen, C$_{1-10}$ alkyl, C$_{1-10}$ alkoxy, C$_{1-10}$ alkylthio, halogen, amino, C$_{1-10}$ alkylamino, di-C$_{1-10}$ alkylamino, C$_{1-10}$ acylamino, aryl, and heteroaryl, with a base in a first polar solvent followed by contacting an activated and hydroxyl-protected 2-deoxy-α-D-erythro-pentofuranosyl compound in a second less polar solvent to form a nucleoside product, (b) contacting the nucleoside product from step (a) with ammonia in a solvent to obtain 2-CdA.

In one example, a method for the preparation of 2-CdA (cladribine) comprises:

(a) contacting a 6-(imidazol-1-yl)purine compound having Formula XXIX:

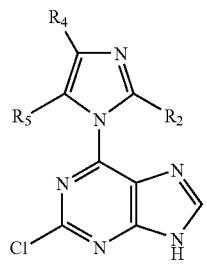

where each of R$_2$, R$_4$ and R$_5$ is independently selected from hydrogen, C$_{1-10}$ alkyl, C$_{1-10}$ alkoxy, C$_{1-10}$ alkylthio, halogen, amino, C$_{1-10}$ alkylamino, di-C$_{1-10}$ alkylamino, C$_{1-10}$ acylamino, aryl, and heteroaryl, with a base in a first polar solvent followed by contacting an activated and hydroxyl-protected 2-deoxy-α-D-erythro-pentofuranosyl compound in a second less polar solvent to form a nucleoside product, (b) alkylating the appended 6-(imidazol-1-yl) ring of the nucleoside product from step (a) for activation of nucleophilic displacement at C-6 of the purine ring, (c) contacting the alkylated 6-(imidazolium) salt from step (b) with ammonia in a third solvent to obtain 2-CdA.

In another example, a method for the preparation of 2-CdA (cladribine) comprises:

(a) contacting a 6-(imidazol-1-yl)purine compound having Formula XXIX:

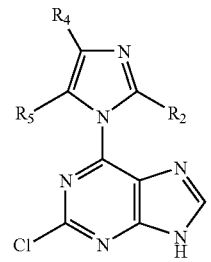

where each of R$_2$, R$_4$ and R$_5$ is independently selected from hydrogen, C$_{1-10}$ alkyl, C$_{1-10}$ alkoxy, C$_{1-10}$ alkylthio, halogen, amino, C$_{1-10}$ alkylamino, di-C$_{1-10}$ alkylamino, C$_{1-10}$ acylamino, aryl, and heteroaryl, with a base in a first polar solvent followed by contacting an activated and hydroxyl-protected 2-deoxy-α-D-erythro-pentofuranosyl compound in a second less polar solvent to form a nucleoside product, (b) contacting the 6-(imidazol-1-yl)purine nucleoside product from step (a) with ammonia in a third solvent to obtain 2-CdA.

In yet another example, a method for the preparation of 2-CdA (cladribine) comprises:

(a) contacting a 6-(1,2,4,-triazol-4-yl)purine compound having Formula XXX:

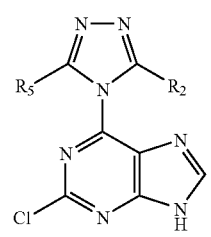

where each of R$_2$ and R$_5$ is independently selected from hydrogen, C$_{1-10}$ alkyl, C$_{1-10}$ alkoxy, C$_{1-10}$ alkylthio, halogen, amino, C$_{1-10}$ alkylamino, di-C$_{1-10}$ alkylamino, C$_{1-10}$ acylamino, aryl, and heteroaryl, with a base in a first polar solvent followed by contacting an activated and hydroxyl-protected 2-deoxy-α-D-erythro-pentofuranosyl compound in a second less polar solvent to form a nucleoside product, (b) alkylating the appended 6-(1,2,4-triazol-4-yl) ring of the nucleoside product from step (a) for activation of nucleophilic displacement at C-6 of the purine ring, (c) contacting the alkylated 6-(triazolium) salt from step (b) with ammonia in a third solvent to obtain 2-CdA.

In still another example, a method for the preparation of 2-CdA (cladribine) comprises:

(a) contacting a 6-(1,2,4,-triazol-1-yl)purine compound having Formula XXX:

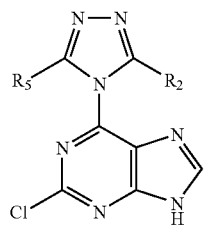

where each of $R_2$ and $R_5$ is independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl, with a base in a first polar solvent followed by reaction with an activated and hydroxyl-protected 2-deoxy-α-D-erythro-pentofuranosyl compound in a second less polar solvent to form a nucleoside product, (b) contacting the 6-(1,2,4-triazol-4-yl)purine nucleoside product from step (a) with ammonia in a third solvent to obtain 2-CdA.

In some of the embodiments, the first polar solvent is a single solvent or a binary solvent mixture with an average dielectric constant of between about 5 and about 40. In other embodiments, the first polar solvent has an average dielectric constant of about 20. In some embodiments, the first polar solvent is acetonitrile. In other embodiments, the first polar solvent is a mixture of acetonitrile and dichloromethane. In other embodiments, the first polar solvent is a mixture of three solvents such as acetonitrile, acetone, tetrahydrofuran, toluene, and the like.

In another aspect of the present invention, a novel method for the preparation of 6-(azolyl)purines is provided. In one embodiment, the invention provides a method for the synthesis of 6-(azolyl)-substituted purines from naturally occurring nucleoside sources, comprising the steps of:

(a) introducing an azolyl substituent at C-6 of a purine nucleoside; and, (b) cleaving the glycosidic bond of the 6-(azolyl)-nucleoside from step (a) to yield a 6-(azolyl)-substituted purine.

In some embodiments, the 6-(azolyl) group is introduced when the glycosyl portion has transiently protected hydroxyl groups.

In some embodiments with a 6-(azolyl) substituent, the azolyl ring is introduced at C-6 of the purine by contacting a purine derivative with an azole under nucleophilic displacement conditions. The leaving group can already be in place at C-6 or can be generated in situ in the reaction medium. Alternatively, the azole can be formed by cyclization of a 6-aminopurine with an azine or a 1,2-diacyl-substituted hydrazine.

Suitable agents for introduction of an azole at C-6 of a purine with a leaving group already at the 6 position include, but are not restricted to, substituted and unsubstituted imidazoles, and substituted and unsubstituted triazoles. Nucleophilic displacement reactions preferably transpire in polar unreactive solvents such as dimethylformamide or acetonitrile at about 15° to about 100° C.

Suitable agents for cyclization reactions to elaborate an azolyl ring at C-6 of a 6-amino purine include 1,2-bis[(dimethylamino)methylene]hydrazine, 1,2-diformylhydrazine, 1,2-diacylhydrazines and the like. Such cyclization reactions preferably transpire in polar unreactive solvents such as dimethylformamide at about 35° to about 200° C.

Suitable agents for replacing the oxo group with an azolyl ring when the purine has a carbonyl group at the 6 position (such as guanine and hypothanine) include, but are not limited to, substituted and unsubstituted imidazoles, substituted and unsubstituted triazoles and the like. Such reactions can be carried out using triphenylphosphine ($Ph_3P$), iodine ($I_2$) and an aprotic base such as diisopropylethylamine (EtN(i-Pr)$_2$), in an aprotic solvent such as toluene at elevated temperatures from about 35° to about 120°.

Suitable agents for cleaving the glycoside bond (deglycosylating agents) of the nucleosides include organic acids, mixtures of organic acids, acid chlorides, and mixtures of organic acids and organic chlorides. In some embodiments, acetic acid, acetyl chloride, or mixtures of acetic acid and acetyl chloride may be used for cleaving the glycoside bonds. Such reagents may be referred to categorically as "a deglycosylating agent."

In one example, a method for preparing 6-(azolyl)-substituted purines comprises deglycosylating a nucleoside of Formula XXXI

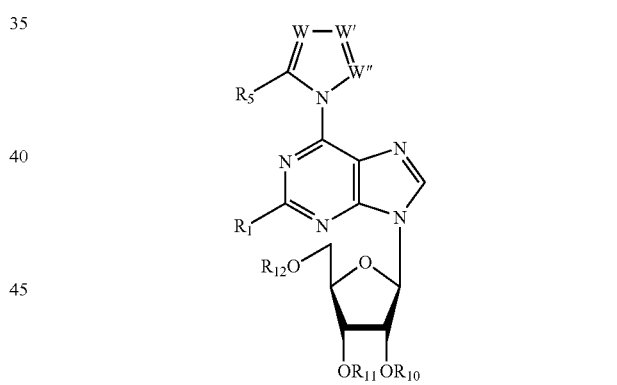

wherein each W, W' and W'' is independently —N—, —CH— or $CR_2$ and at least one of W, W' and W'' is —N—, $R_1$, $R_2$ and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl, each of $R_{10}$, $R_{11}$ and $R_{12}$ are hydroxyl protecting groups, with a deglycosylating agent. In some examples, the hydroxyl protecting groups may be acyl, acetal, ketal, allylic or vinylic "alkyl", substituted silyl (such as tert-butyldimethylsilyl) and others well known to persons skilled in the art.

In one embodiment, a method of preparing 6-(imidazol-1-yl)-substituted purines comprises deglycosylating a nucleoside of Formula XXXII

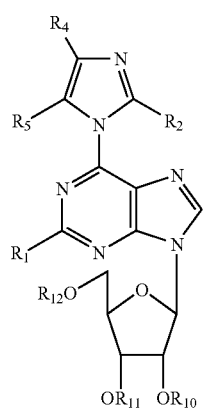

wherein $R_1$, $R_2$, $R_4$ and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl, and each of $R_{10}$, $R_{11}$ and $R_{12}$ are hydroxyl protecting groups, with a deglycosylating agent. In some examples, the hydroxyl protecting groups may be acyl, acetal, ketal, allylic or vinylic "alkyl", substituted silyl (such as tert-butyldimethylsilyl) and others well known to persons skilled in the art.

The 6-(imidazol-1-yl)purines can be prepared from inosine according to procedures shown in Scheme 3. The substituted-imidazoles can be prepared either by alkylation or cyclization

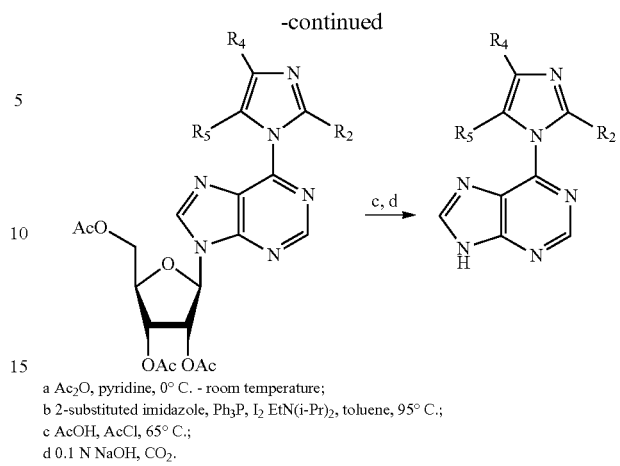

a Ac$_2$O, pyridine, 0° C. - room temperature;
b 2-substituted imidazole, Ph$_3$P, I$_2$ EtN(i-Pr)$_2$, toluene, 95° C.;
c AcOH, AcCl, 65° C.;
d 0.1 N NaOH, CO$_2$.

The 2-chloro-6-(imadzol-1-yl)purines can be prepared from guanosine according to procedures shown in Scheme 4. The substituted-imidazoles can be prepared either by alkylation or cyclization.

Scheme 4

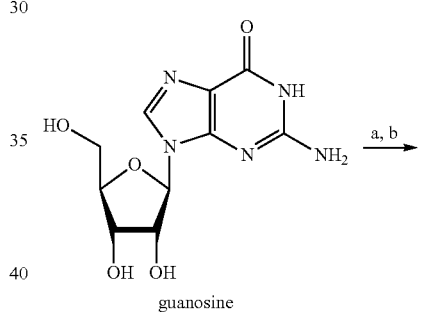

guanosine

Scheme 3

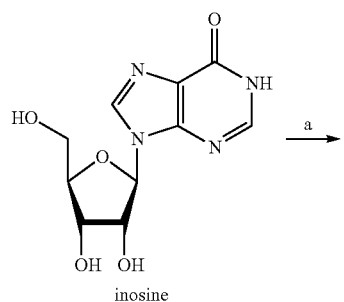

inosine

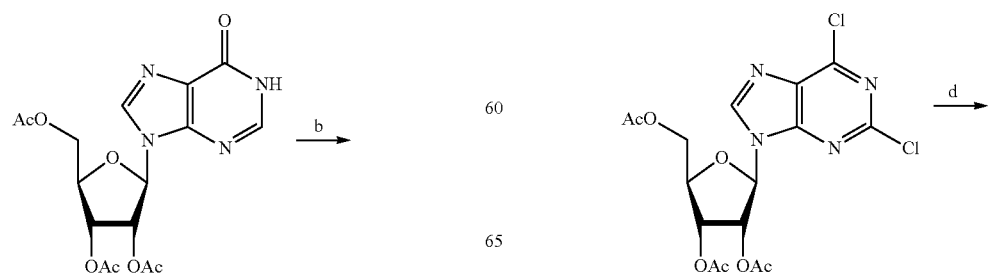

-continued

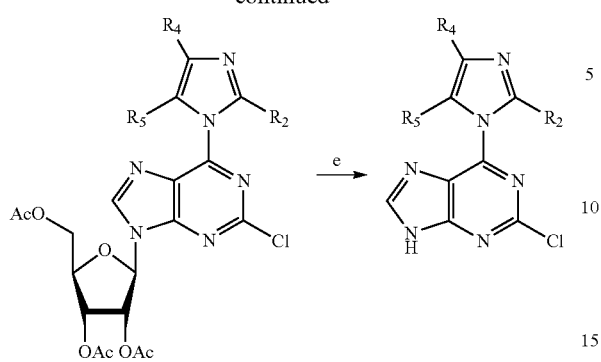

a Ac₂O, DMF, pyridine, 75° C.;
b POCl₃, PhNMe₂, BnEt₃NCl, acetonitrile, reflux;
c TMSCl, TEBANO₂, dichloromethane, room temperature;
d imidazoles, acetonitrile, room temperature;
e AcCl, AcOH, 65° C.;

Examples of 2-chloro-6-(substituted-imidazol-1-yl)purines prepared according to Scheme 4 in Table 2. The overall yield for steps a-c is 74%.

TABLE 2

| $R_2$, $R_4$, $R_5$ | % Yield (combined steps d and e) |
|---|---|
| CH(CH₃)₂(isopropyl), H, H | 54 |
| CH₂CH₂CH₃(propyl), H, H | 82 |
| CH₂CH₂CH₂CH₃(butyl), H, H | 57 |
| CH₂CH₂CH₂CH₂CH₃(pentyl), H, H | 48 |
| CH₂CHPhCH₃(2-phenylpropyl), H, H | 62 |
| H, Ph, Ph | 61 |
| CH₂Ph(benzyl), H, H | 62 |

In another embodiment, a method of preparing 6-(1,2,4-triazol-4-yl)-substituted purines comprises deglycosylating a nucleoside of Formula XXXIII

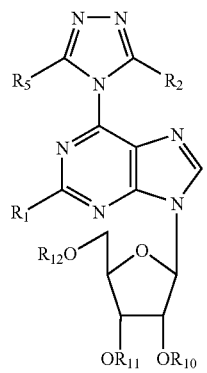

wherein each R group is defined as above, and contacted with a deglycosylating agent.

In another aspect of the present invention, a novel method for the preparation of 6 substituted purines is provided. In one embodiment, the invention provides a method for the synthesis of 6-substituted purines from purine sources, comprising introduction of an azolyl ring at the 6 position of a purine. The 6-substituted purine may have the Formula I

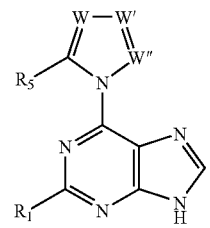

where W, W', W" and the R groups have the definitions previously described.

In some embodiments with a 6-(azolyl)purine, the azole ring is introduced at C-6 of the purine by contacting the purine with an azole under nucleophilic displacement conditions using conditions analogous to those previously described. Alternatively, the azole can be formed by cyclization of a 6-aminopurine with an azine or substituted hydrazine using conditions analogous to those previously described.

In some embodiments, 6-(imidazol-1-yl)purines can be prepared from hypoxanthine according to procedures shown in Scheme 5. The 2-substituted imidazoles can be prepared either by alkylation or cyclization.

Scheme 5

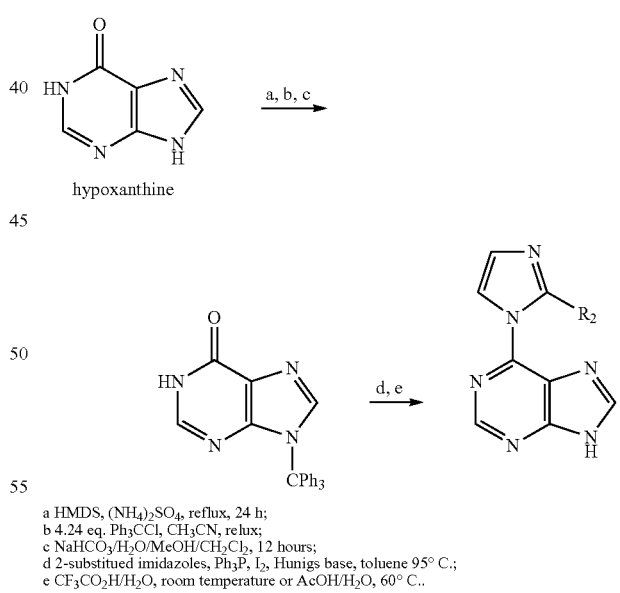

a HMDS, (NH₄)₂SO₄, reflux, 24 h;
b 4.24 eq. Ph₃CCl, CH₃CN, relux;
c NaHCO₃/H₂O/MeOH/CH₂Cl₂, 12 hours;
d 2-substitued imidazoles, Ph₃P, I₂, Hunigs base, toluene 95° C.;
e CF₃CO₂H/H₂O, room temperature or AcOH/H₂O, 60° C..

In another example, 2-chloro-6-(2-alkylimidazol-1-yl)purines can be prepared by contacting 2,6-dichloropurine with 2-substituted imidazoles in DMF at 65° C.

In yet another example, 2-amino-6-(imidazol-1-yl)purine and 2-acetamido-6-(imidazol-1-yl)purine can be prepared according to procedures described in Scheme 6 below.

Scheme 6

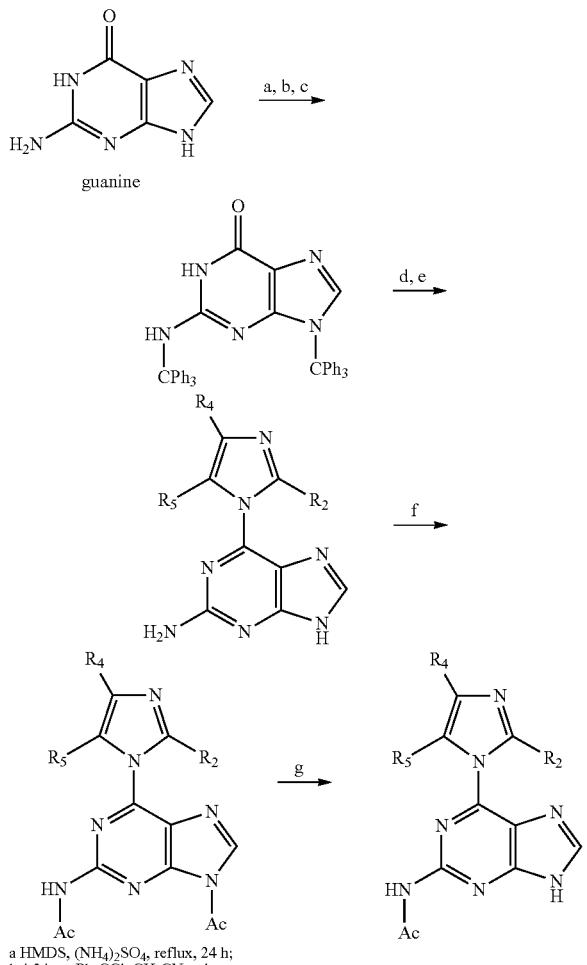

a HMDS, (NH$_4$)$_2$SO$_4$, reflux, 24 h;
b 4.24 eq. Ph$_3$CCl, CH$_3$CN, relux;
c NaHCO$_3$/H$_2$O/MeOH/CH$_2$Cl$_2$, 12 hours;
d 2,4,5-substitued imidazoles, Ph$_3$P, I$_2$, Hunigs base, toluene 95° C.;
e CF$_3$CO$_2$H/H$_2$O, room temperature or AcOH/H$_2$O, 60° C.;
f Ac$_2$O, DMF 150° C.;
g MeOH, reflux, or NaHCO$_3$/H$_2$O saturated, room temperature or EtOH, reflux.

The maximum dihedral angle tolerated between the planes of the purine ring and the appended azole ring at C-6 while still resulting in regiospecific glycosylation depends upon the nature of the electrophile (glycosylating agent). The more bulky and more reactive the electrophile, the further from coplanarity the 6-(azolyl) ring and the purine ring can be and still result in formation of regiospecific products. The less bulky and less reactive the electrophile, the closer to coplanarity these rings must be to result in regiospecific products. For example, glycosylation of the sodium salt of 2-chloro-6-(4,5,-diphenylimidazol-1-yl)purine with the bulky and reactive 2-deoxy-3,5-di-O-(p-toluoyl)-α-D-erythro-pentofuranosyl chloride gives the N-9 glycosylated product exclusively in quantitative yield, whereas treatment of the sodium salt of 2-chloro-6-(4,5,-diphenylimidazol-1-yl)purine with the smaller and less reactive ethyl iodide in DMF gives both the N-9 and N-7 alkylated products in a ratio of about 5:1 (N-9: N-7) in quantitative yield.

In yet another aspect of the invention, novel 6-(azolyl) purine compounds are provided. The 6-(azolyl) groups are useful for directing regiospecific and regioselective N-9 glycosylation reactions to provide therapeutic agents.

In one example, a compound of Formula I is provided

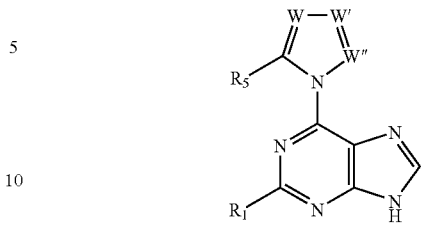

where each W, W' and W" is independently selected from —N—, —CH— and CR$_2$, and where at least one of W, W' and W" is —N—, and where R$_1$, R$_2$, and R$_5$ are independently selected from hydrogen, C$_{1-10}$ alkyl, C$_{1-10}$ alkoxy, C$_{1-10}$ alkylthio, halogen, amino, C$_{1-10}$ alkylamino, di-C$_{1-10}$ alkylamino, C$_{1-10}$ acylamino, aryl, and heteroaryl, and pharmaceutically acceptable salts of these compounds, provided that:

(1) when R$_1$ is amino and both W and W' are N, then R$_5$ is not hydrogen;

(2) when R$_1$ is hydrogen and W' and W" are CH, then R$_5$ is not hydrogen;

(3) when R$_1$ is hydrogen and R$_5$ is methyl, then W' and W" are not CH;

(4) when R$_1$ and R$_5$ are hydrogen and W' is CCH$_3$, then W" is not CH;

(5) when R$_1$ and R$_5$ are hydrogen and W' is CH, then W" is not N;

(6) when R$_1$ and R$_5$ are hydrogen and W" is N, then W and W' are not CH;

(7) when R$_1$ and R$_5$ are hydrogen and W" is N, then W is not CCH$_3$;

(8) when R$_1$ and R$_5$ are hydrogen and W" is N, then W' is not CCH$_3$.

In another example, a compound of Formula XV is provided where R$_1$, R$_2$, R$_4$ and R$_5$ are independently selected from hydrogen, C$_{1-10}$ allyl, C$_{1-10}$ alkoxy, C$_{1-10}$ alkylthio, halogen, amino, C$_{1-10}$ alkylamino, di-C$_{1-10}$ alkylamino, C$_{1-10}$ acylamino, aryl, and heteroaryl, and pharmaceutically acceptable salts of these compounds, provided that:

(1) when R$_1$, R$_2$ and R$_4$ are hydrogen, then R$_5$ is not hydrogen;

(2) when R$_1$, R$_2$ and R$_5$ are hydrogen, then R$_4$ is not methyl;

(3) when R$_1$, R$_4$ and R$_5$ are hydrogen, then R$_2$ is not methyl.

In still another example, a compound of Formula XXII is provided

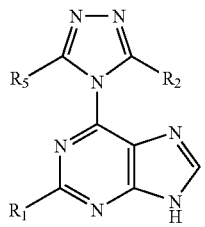

where $R_1$, $R_2$, and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl, and pharmaceutically acceptable salts of these compounds; provided that when $R_1$ is amino, then at least one of $R_2$ and $R_5$ is not hydrogen.

In yet another example, a compound of Formula XXXIV is provided

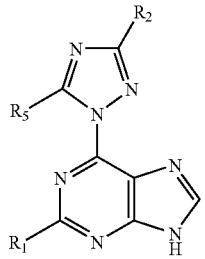

where $R_1$, $R_2$, and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl, and pharmaceutically acceptable salts of these compounds; provided that when $R_1$ is hydrogen, then at least one of $R_2$ and $R_5$ is not hydrogen.

In another example, a compound of Formula XXXV is provided

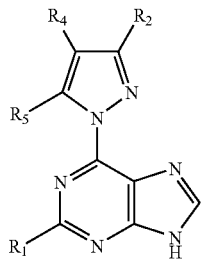

where $R_1$, $R_2$, $R_4$ and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl, and pharmaceutically acceptable salts of these compounds; provided that:

(1) when $R_1$ is hydrogen, then at least one of $R_2$, $R_4$ and $R_5$ is not hydrogen;

(2) when $R_1$, $R_2$ and $R_5$ are hydrogen, then $R_4$ is not methyl;

(3) when $R_1$, $R_4$ and $R_5$ are hydrogen, then $R_2$ is not methyl.

In another example, a compound of Formula XXXVI is provided

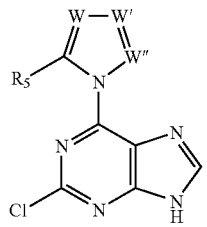

where each W, W' and W" is independently selected from —N—, —CH— or $CR_2$ and at least one of W, W' and W" is —N—, $R_2$ and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl, and pharmaceutically acceptable salts of these compounds.

EXAMPLES

General Method 1

6-(azolyl)purine glycosylation

A mixture of the 6-(azolyl)purine (1 mmol) and sodium hydride (0.06 g, 60% w/w suspension, 1.5 mmol) in a dried polar solvent (A) was stirred at ambient temperature under $N_2$ for 2 h. A solution of 2-deoxy-3,5-di-O-(p-toluoyl)-α-D-erythro-pentofuranosyl chloride (1.8 mmol) in a less polar dried solvent (B) was added with a syringe. The mixture was stirred for 22 h, and volatiles were evaporated in vacuo.

General Method 2

6-(azolyl)purine glycosylation

A mixture of a 6-(2-alkylimidazol-1-yl)-2-chloropurine (1 mmol) and sodium hydride (60% w/w suspension, 1.5 mmol) in dried $CH_3CN$ (10 mL) was stirred at ambient temperature under $N_2$ for 8 h. The solution was chilled to 0° C., and a solution of 2-deoxy-3,5-di-O-p-toluoyl)-α-D-erythro-pentofuranosyl chloride (1.8 mmol) in cold, dried $CH_2Cl_2$ (10 mL, 0° C.) was added with a syringe. The reaction mixture was then stirred for 22 h, and allowed to gradually warm to ambient temperature. Volatiles were evaporated in vacuo and the residue was chromatographed (25 g silica gel, MeOH/$CH_2Cl_2$, 1:30).

General Method 3

Alkylation of the 6-(azolyl) Ring and Ammonolysis

The 6-(2-allylimidazol-1-yl)-2-chloro-9-[2-deoxy-3,5-di-O-(p-toluoyl)-β-D-erythro-pentofuranosyl]purine (1 mmol) was added to 0.3 M BnI/$CH_3CN$ (40 mL, 12 mmol), which was prepared in situ from NaI (15 g, 94 mmol) and BnCl (3.5 mL, 3.85 g, 30.4 mmol) in $CH_3CN$ (100 mL). The mixture was stirred at 60° C. for 1.5 h. Removal of volatiles and chromatography (MeOH/$CH_2Cl_2$, 1:90→1:30) gave the benzylimidazolium iodide salt as yellow foam, which was transferred into a pressure flask and cooled at −4° C. Cold $NH_3$/MeOH (26%, 50 mL) was added, and the sealed mixture was stirred at 60° C. for 11 h. Volatiles were evaporated, and the residue was chromatographed [Dowex 1×2 (OH⁻) resin, $H_2O$/MeOH, 1:0→3:2] to give 2-chloro-2'-deoxyadenosine.

Preparation of 2-propylimidazole

To a suspension of $NH_4HCO_3$ (16.45 g, 208.1 mmol) in $H_2O$ (10 mL) was added butyraldehyde (9.2 mL, 7.52 g, 104 mmol) and glyoxal/$H_2O$ (40% w/w, 11.9 mL, 15.09 g, 104.0 mmol). The mixture was stirred at ambient temperature overnight, and volatiles were evaporated. The residue was extracted with THF. The extracts were combined, and volatiles were evaporated to give the crude material (11 g, 96%), which was chromatographed ($CH_2Cl_2 \to MeOH/CH_2Cl_2$, 1:60→1:30) to give 2-propylimidazole (7.45 g, 65%): $^1$H NMR (500 MHz, $CDCl_3$) δ 11.50 (s, 1H), 6.96 (s, 2H), 2.72 (t, J=7.4 Hz, 2H), 1.77 (sext, J=7.4 Hz, 2H), 0.98 (t, J=7.4 Hz, 3H); $^{13}$C NMR (125 MHz, $CDCl_3$) δ 149.1, 121.4, 30.7, 22.3, 14.0.

Preparation of 6-(2-propylimidazol-1-yl)purine

A suspension of 2',3',5'-tri-O-acetylinosine (1.58 g, 4.0 mmol), 2-propylimidazole (1.60 g, 14.4 mmol), $Ph_3P$ (2.58 g, 9.6 mmol), $I_2$ (2.14 g, 8.32 mmol), and $EtN(i-Pr)_2$ (3.6 mL, 2.67 g, 20.2 mmol) in dried toluene (40 mL) was stirred at 95° C. for 4 h. Volatiles were evaporated in vacuo, and the residue was extracted with boiling EtOAc. The combined extracts were evaporated to dryness, and the residue was chromatographed ($CH_2Cl_2$/MeOH, 1:40) to give a solid contaminated with $Ph_3PO$. This material was dissolved in AcOH (160 mL), and AcCl (2.2 mL, 2.43 g, 31 mmol) was added. The solution was stirred at 65° C. overnight, and volatiles were evaporated in vacuo. The residue was dissolved in $CH_2Cl_2$ and extracted with 0.1 N NaOH/$H_2O$. The aqueous layer was washed ($CH_2Cl_2$), and precipitation with $CO_2$ followed by filtration and thorough washing ($H_2O$) gave a solid (0.66 g, 72%). This material was dissolved in MeOH and decolorized with charcoal. Recrystallization (MeOH) gave 6-(2-propylimidazol-1-yl)purine as a colorless solid: mp 242.5-243.5° C.; UV (MeOH) max 278 nm (∈ 13 700), min 235 nm (∈ 5000); $^1$H NMR (300 MHz, DMSO-$d_6$) δ 13.90 (br s, 1H), 8.86 (s, 1H), 8.69 (s, 1H), 8.36 (s, 1H), 7.07 (d, J=1.5 Hz, 1H), 3.18 (t, J=7.3 Hz, 2H), 1.72 (sext, J=7.3 Hz, 2H), 0.93 (t, J=7.3 Hz, 3H); $^{13}$C NMR (75 MHz, $CDCl_3$) δ 155.5, 152.0, 149.8, 146.9, 145.8, 128.5, 123.6, 121.4, 32.2, 21.5, 14.5; HRMS m/z 228.1109 ($M^+[C_{11}H_{12}N_6]$=228.1123). Anal. Calcd for $C_{11}H_{12}N_6$: C, 57.88; H, 5.30; N, 36.82. Found: C, 58.09; H, 5.19; N, 37.00.

Preparation of 2-chloro-6-(2-propylimidazol-1-yl purine

Method 1:

2,6-Dichloropurine (0.38 g, 2 mmol) and 2-propylimidazole (1.32 g, 12 mmol) were dissolved in freshly distilled DMF (10 mL), and the mixture was stirred at 65° C. for 20 h. Volatiles were evaporated in vacuo, and the residue was dissolved in 0.1 N NaOH/$H_2O$//$CH_2Cl_2$ (100 mL/50 mL). The organic phase was extracted with 0.1 N NaOH/$H_2O$ (3×50 mL). The combined aqueous phase was washed with $CH_2Cl_2$ (2×50 mL) and neutralized with $CO_2$. The precipitated solid was filtered and washed ($H_2O$) to give 2-chloro-6-(2-propylimidazol-1-yl)purine (0.38 g, 72%): mp 224.5-225° C.; UV (MeOH) max 215, 288 nm (∈ 25 800, 16 700), min 332, 241 nm (∈ 2500, 4500); $^1$H NMR (500 MHz, DMSO-$d_6$) δ 14.04 (br s, 1H), 8.69 (s, 1H), 8.43 (s, 1H), 7.06 (s, 1H,), 3.12 (t, J=7.5 Hz, 2H), 1.72 (sext, J=7.3 Hz, 2H), 0.95 (t, J=7.3 Hz, 3H); $^{13}$C NMR (125 MHz, DMSO-$d_6$) δ 157.3, 151.7, 150.2, 147.2, 146.6, 128.9, 122.5, 121.1, 32.4, 21.5, 14.5; HRMS m/z 262.0723 ($M^+[C_{11}H_{11}ClN_6]$=262.0734). Anal. Calcd for $C_{11}H_{11}ClN_6$: C, 50.29; H, 4.22; N, 31.99. Found: C, 50.02; H, 4.28; N, 31.64.

Method 2:

Preparation of 9-(2,3,5-tri-O-acetyl-β-D-ribofuranosyl)-2-chloro-6-(2-propylimidazol-1-yl)purine Method A:

A mixture of 2',3',5'-tri-O-acetyl-2-N-tritylguanosine (5.92 g, 9.1 mmol), $I_2$ (11.55 g, 45.5 mmol), $Ph_3P$ (11.93 g, 45.5 mmol) and 2-propylimidazole (5.01 g, 45.5 mmol) was stirred in toluene (180 mL) at 95° C. for 15 min. DIPEA (15.9 mL, 11.80 g, 91.3 mmol) was added, and the mixture was stirred at 95° C. overnight. After removal of volatiles in vacuo, the residue was extracted with boiling EtOAc. The combined EtOAc extracts were evaporated to dryness, and the residue was dried under vacuum. The material obtained was stirred in TFA/$H_2O$ (9:1, 250 mL) at 0° C. for 4 h. Volatiles were evaporated in vacuo, and the residue was chromatographed ($CH_2Cl_2 \to MeOH/CH_2Cl_2$, 1:12). This solid material was treated with charcoal in MeOH. Volatiles were evaporated in vacuo, and the residue was dissolved in $CH_2Cl_2$ and washed ($NaHCO_3$/$H_2O$, brine) and dried ($Na_2SO_4$) to give 9-(2,3,5-tri-O-acetyl-β-D-ribofuranosyl)-2-amino-6-(2-propylimidazol-1-yl)purine as a colored solid (3.20 g, 81%, contaminated with $Ph_3PO$).

To a stirred solution of 9-(2,3,5-tri-O-acetyl-β-D-ribofuranosyl)-2-amino-6-(2-propylimidazol-1-yl)purine (2.37 g, 4.72 mmol) in $CH_2Cl_2$ (120 mL) was added TMSCl (5.3 mL, 4.54 g, 42.5 mmol) dropwise under $N_2$, and then $BTEANO_2$ (7.1 g, 29.8 mmol) in $CH_2Cl_2$ (40 mL). Evolution of gas was observed, and when this subsided, additional TMSCl (5.3 mL) was added. The mixture was then stirred at ambient temperature for 3 h. The solution was diluted with $CH_2Cl_2$ and washed ($NaHCO_3$/$H_2O$, 2×200 mL+100 mL), and the aqueous layer was extracted with $CH_2Cl_2$. The combined organic phase was dried ($Na_2SO_4$), and volatiles were evaporated in vacuo. The residue was chromatographed (MeOH/$CH_2Cl_2$, 1:99-1:90) to give crude product (1.40 g, 57%, contaminated with $Ph_3PO$), which was recrystallized (i-PrOH) to give 9-(2,3,5-tri-O-acetyl-β-D-ribofuranosyl)-2-chloro-6-(2-propylimidazol-1-yl)purine: mp 126-127.5° C.; UV (MeOH) max 217, 287 nm (∈ 25 300, 15 000), min 238, 261 nm (∈ 4200, 6200); $^1$H NMR (500 MHz, $CDCl_3$) δ 8.57 (d, J=1.8 Hz, 1H), 8.25 (s, 1H), 7.11 (d, J=1.5 Hz, 1H), 6.27 (d, J=5.5 Hz, 1H), 5.83 (t, J=5.5 Hz, 1H), 5.60-5.62 (m, 1H), 4.49-4.51 (m, 1H), 4.43-4.44 (m, 2H), 3.29 (t, J=7.7 Hz, 2H), 2.19 (s, 3H), 2.17 (s, 3H), 2.11 (s, 3H), 1.86 (sext, J=7.6 Hz, 2H), 1.07 (t, J=7.7 Hz, 3H); $^{13}$C NMR (125 MHz, $CDCl_3$) δ 170.5, 169.9, 169.7, 154.6, 153.8, 151.6, 148.4, 142.5, 129.3, 123.0, 120.5, 86.6, 81.0, 73.5, 70.8, 63.2, 33.2, 21.6, 21.1, 20.8, 20.7, 14.2; HRMS m/z 520.1476 ($M^+[C_{22}H_{25}ClN_6O_7]$= 520.1473). Anal. Calcd For $C_{22}H_{25}ClN_6O_7$: C, 50.73; H, 4.84; N, 16.13. Found: C, 50.58; H, 4.87; N, 16.15.

Method B:

A mixture of 9-(2,3,5-tri-O-acetyl-β-D-ribofuranosyl)-2,6-dichloropurine (1.12 g, 2.5 mmol) and 2-propylimidazole (2.20 g, 20 mmol) was dissolved in $CH_3CN$ (30 mL) and stirred at 65° C. under $N_2$ for 2 h (reaction complete, TLC). After removal of volatiles, the residue was dissolved in $CH_2Cl_2$ (200 mL) and washed ($H_2O$, 3×50 mL). The aqueous phase was extracted with $CH_2Cl_2$, and the combined organic phase was dried ($Na_2SO_4$) and evaporated to dryness. The residue was chromatographed (MeOH/$CH_2Cl_2$, 1:95) to give 9-(2,3,5-tri-O-acetyl-β-D-ribofuranosyl)-2-chloro-6-(2-propylimidazol-1-yl)purine (977 mg, 93%).

An extended reaction time (20 h) caused minor formation of bis-substituted product: LRMS m/z 594 (M+ [$C_{28}H_{34}N_8O_7$]=594).

9-(2,3,5-Tri-O-acetyl-β-D-ribofuranosyl)-2-chloro-6-(2-propylimidazol-1-yl)purine (4.99 g, 9.6 mmol) was dissolved in HOAc (400 mL). To the solution was added AcCl (4.0 mL, 4.42 g, 56.3 mmol), and the mixture was stirred at 65° C. for 1.5 h in a sealed flask (reaction almost complete, TLC). Volatiles were evaporated in vacuo, and the residue was washed ($CH_2Cl_2$), and dissolved in 0.1 N NaOH/$H_2O$. Precipitation with $CO_2$ gave 2-chloro-6-(2-propylimidazol-1-yl)purine (2.20 g, 88%). Recrystallization (MeOH) gave the pure material (1.93 g, 77%).

Preparation of
2-chloro-6-(2-isopropylimidazol-1-yl)purine 9-(2,3,5-Tri-O-acetyl-β-D-ribofuranosyl)-2-chloro-6-(2-isopropylimidazol-1-yl)purine (2.96 g, 5.7 mmol, contaminated with 2-isopropylimidazole) was dissolved in HOAc (190 mL). To the solution was added AcCl (1.9 mL, 2.10 g, 26.7 mmol), and the mixture was stirred at 65° C. for 20 h in a sealed flask (reaction was complete, TLC). Volatiles were evaporated in vacuo, and the residue was washed ($CH_2Cl_2$) and dissolved in 0.1 N NaOH/$H_2O$ (200 mL). Precipitation with $CO_2$ gave 2-chloro-6-(2-isopropylimidazol-1-yl)purine (0.675 g, 54%). This solid was washed (boiling MeOH/iPrOH) to give the title compound (0.60 g, 48%): mp 268-268.5° C.; UV (MeOH) max 213, 254, 288 nm (∈ 26 100, 4600, 13 100), min 239, 257 nm (∈ 3700, 4600); $^1$H NMR (500 MHz, DMSO-$d_6$) δ 14.06 (s, 1H), 8.71 (s, 1H), 8.36 (s, 1H), 7.07 (d, J=1.6 Hz, 1H), 3.93 (br s, 1H), 1.29 (d, J=6.8 Hz, 6H); $^{13}$C NMR (125 MHz, DMSO-$d_6$) δ 156.4, 154.3, 151.0, 146.5, 145.8, 127.9, 122.0, 120.4, 27.7, 21.6; HRMS m/z 285.0626 (MNa+[$C_{11}H_{11}ClN_6Na$]=285.0631). Anal. Calcd for $C_{11}H_{11}ClN_6$: C, 50.29; H, 4.22; N, 31.99. Found: C, 50.12; H, 4.27; N, 32.16.

Preparation of
6-(2-butylimidazol-1-yl)-2-chloropurine

A solution of 9-(2,3,5-tri-O-acetyl-β-D-ribofuranosyl)-2,6-dichloropurine (2.41 g, 5.4 mmol) and 2-butylimidazole (6.68 g, 54 mmol) in $CH_3CN$ (60 mL) was stirred at 65° C. under $N_2$ for 32 h (reaction complete, TLC). Volatiles were evaporated in vacuo, and the residue was chromatographed (MeOH/$CH_2Cl_2$, 1:90) to give crude 9-(2,3,5-tri-O-acetyl-β-D-ribofuranosyl)-6-(2-butylimidazol-1-yl)-2-chloropurine (3.33 g, contaminated with 2-butylimidazole): $^1$H NMR (500 MHz, $CDCl_3$) δ 8.56 (s, 1H), 8.24 (s, 1H), 7.10 (s, 1H), 6.26 (d, J=5.8 Hz, 1H), 5.83 (t, J=5.6 Hz, 1H), 5.61 (t, J=5.6 Hz, 1H), 4.43-4.51 (m, 3H), 3.31 (t, J=7.9 Hz, 2H), 2.18 (s, 3H), 2.16 (s, 3H), 2.11 (s, 3H), 1.81 (quint, J=7.7 Hz, 2H), 1.50 (sext, J=7.7 Hz, 2H), 0.98 (t, J=7.3 Hz, 3H); HRMS m/z 535.1702 (MH+[$C_{23}H_{28}ClN_6O_7$]=535.1708).

Crude 9-(2,3,5-tri-O-acetyl-β-D-ribofuranosyl)-6-(2-butylimidazol-1-yl)-2-chloropurine (2.16 g, 4 mmol) was dissolved in acetic acid (167 mL). To the solution was added AcCl (1.67 mL, 1.84 g, 23.5 mmol), and the mixture was stirred at 65° C. for 23 h in a sealed flask (reaction complete, TLC). Volatiles were evaporated in vacuo, and the residue was washed ($CH_2Cl_2$) and dissolved in 0.1 N NaOH/$H_2O$ (130 mL). Precipitation with $CO_2$ gave a solid (0.76 g, 57%) that was recrystallized (MeOH) to give 6-(2-butylimidazol-1-yl)-2-chloropurine (0.58 g, 44%): mp 247-247.5° C.; UV (MeOH) max 214, 254, 288 nm (∈ 25 600, 4700, 13 900), min 239, 257 nm (∈ 3800, 4600); $^1$H NMR (500 MHz, DMSO-$d_6$) δ 14.05 (s, 1H), 8.71 (s, 1H), 8.44 (s, 1H), 7.07 (d, J=1.5 Hz, 1H), 3.17 (t, J=7.7 Hz, 2H), 1.70 (quint, J=7.6 Hz, 2H), 1.39 (sext, J=7.6 Hz, 2H), 0.91 (t, J=7.4 Hz, 3H); $^{13}$C NMR (125 MHz, DMSO-$d_6$) δ 156.3, 151.0, 149.5, 146.4, 145.7, 128.1, 121.7, 120.3, 29.5, 29.3, 21.9, 13.6; HRMS m/z 277.0973 (MNa+[$C_{12}H_{14}ClN_6Na$]=277.0968). Anal. Calcd for $C_{12}H_{14}ClN_6$: C, 52.08; H, 4.74; N, 30.37. Found: C, 51.96; H, 4.85; N, 30.52.

Preparation of
2-chloro-6-(2-hexylimidazol-1-yl)purine

A sample of 2,6-dichloropurine (0.19 g, 1 mmol) and 2-hexylimidazole (0.97 g, 6.36 mmol) were dissolved in freshly distilled DMF (20 mL), and the mixture was stirred at 65° C. for ~20 h (reaction incomplete, TLC). Volatiles were evaporated in vacuo, and the residue was dissolved in HOAc (5 mL), and volatiles were evaporated. The residue was chromatographed (MeOH/$CH_2Cl_2$, 1:30) to give a solid contaminated with both starting materials. This solid was washed thoroughly with $CH_2Cl_2$, then saturated $NaHCO_3$/$H_2O$ to give 2-chloro-6-(2-hexylimidazol-1-yl)purine (0.17 g, 56%): mp 192-193° C.; UV (MeOH) max 214, 288 nm (∈ 25 900, 41 200), min 240 nm (∈ 4500); $^1$H NMR (500 MHz, DMSO-$d_6$) δ 14.03 (br, 1H), 8.70 (s, 1H), 8.42 (s, 1H), 7.06 (s, 1H), 3.16 (t, J=7.7 Hz, 2H), 1.69 (quint, J=7.3 Hz, 2H), 1.39-1.33 (m, 2H), 1.22-1.30 (m, 4H), 0.84 (t, J=7.0 Hz, 3H); $^{13}$C NMR (500 MHz, DMSO-$d_6$) δ 157.3, 151.7, 150.3, 147.2, 146.7, 128.9, 122.6, 121.1, 31.7, 31.4, 30.4, 29.2, 28.2. 22.7; HRMS m/z 304.1185 (M [$C_{14}H_{17}ClN_6$]=304.1203).

Preparation of
2-chloro-6-[2-(2-phenylpropyl)imidazol-1-yl]purine

A mixture of 9-(2,3,5-tri-O-acetyl-β-D-ribofuranosyl)-2,6-dichloropurine (0.98 g, 2.19 mmol) and 2-(2-phenylpropyl)imidazole (4.07 g, 21.9 mmol) in $CH_3CN$ (20 mL) was stirred at 65° C. for 17 h (reaction complete, TLC). Volatiles were evaporated in vacuo, and the residue was chromatographed (MeOH/$CH_2Cl_2$, 1:90) to give a mixture of diastereomers (quantitative, contaminated with 2-(2-phenylpropyl)imidazole). The mixture was dissolved in HOAc (91 mL), and to the solution was added AcCl (0.92 mL, 1.00 g, 12.8 mmol). The mixture was stirred at 65° C. for 25.5 h in a sealed flask (reaction complete, TLC). Volatiles were evaporated in vacuo, and the residue was dissolved in 0.1 N NaOH/$H_2O$ (300 mL) and $CHCl_3$ (150 mL). The mixture was stirred for 2 h, and then neutralized with $CO_2$. The organic phase was separated, and the aqueous phase was extracted with $CH_2Cl_2$. The combined organic phase was dried ($Na_2SO_4$) and concentrated to dryness. The residue was washed ($H_2O$), suspended in EtOH, and filtered to give 2-chloro-6-[2-(2-phenylpropyl)imidazol-1-yl]purine (0.46 g, 62%) of material. The mother liquor was evaporated to dryness, and the residue was chromatographed (MeOH/$CH_2Cl_2$, 1:30→1:12) to give a solid, which was washed ($H_2O$) to give the second crop (0.18 g, 86% total). The combined solids were dissolved in 0.1 N NaOH/$H_2O$ (300 mL). Precipitation with $CO_2$ gave 2-chloro-6-[2-(2-phenylpropyl)imidazol-1-yl]purine as an enantiomeric mixture (0.59 g, 80%): mp 258.5-259° C.; UV (MeOH) max 254, 289 nm (∈ 12 000, 4100), min 240, 256 nm (F 3600, 4100); $^1$H NMR (500 MHz, DMSO-$d_6$) δ 14.00 (s, 1H), 8.68 (s, 1H), 8.35 (s, 1H), 7.13-7.14 (m, 4H), 7.07 (d, J=1.9 Hz, 1H), 7.00-7.04 (m, 1H), 3.58 (dd, J=14.4, 6.7 Hz, 1H), 3.43 (dd, J=14.2, 7.7 Hz, 1H), 3.30 (sext, J=7.0 Hz, 1H), 1.23 (1.22) (s, 3H); $^{13}$C NMR (125 MHz, DMSO-$d_6$) δ 156.4, 150.9, 147.9, 146.4, 145.8, 145.7, 128.2, 127.9, 126.6, 125.7, 121.7, 120.5, 38.3, 37.7, 21.0; HRMS m/z 361.0935 (MNa$^+$ [C$_{17}$H$_{15}$ClN$_6$Na]=361.0944). Anal. Calcd for C$_{17}$H$_{15}$ClN$_6$: C, 60.27; H, 4.46; N, 24.81. Found: C, 60.12; H, 4.60; N, 24.66.

Preparation of
2-chloro-6-(4,5-diphenylimidazol-1-yl)purine

A solution of 9-(2,3,5-tri-O-acetyl-β-D-ribofuranosyl)-2,6-dichloropurine (0.45 g, 1.0 mmol) and 4,5-diphenylimidazole (2.21 g, 10 mmol) in DMF (15 mL) was stirred at 65° C. under N$_2$ for 67 h (reaction almost complete, TLC). Volatiles were evaporated in vacuo, and the residue was chromatographed (MeOH/CH$_2$Cl$_2$, 1:90) to give 9-(2,3,5-tri-O-acetyl-β-D-ribofuranosyl)-2-chloro-6-(4,5-diphenylimidazol-1-yl) purine (0.53 g, 83%) and a mixture of 4,5-diphenylimidazole (19 mg) and the title compound (52 mg, 91% total). Recrystallization (iPrOH) gave 9-(2,3,5-tri-O-acetyl-β-D-ribofuranosyl)-2-chloro-6-(4,5-diphenylimidazol-1-yl)purine: mp 146-146.5° C.; UV (MeOH) max 279 nm (∈ 18 300), min 267 nm (∈ 16 800); $^1$H NMR (500 MHz, CDCl$_3$) δ 9.03 (s, 1H), 8.22 (s, 1H), 7.55-7.57 (m, 2H), 7.35-7.40 (m, 4H), 7.21-7.27 (m, 4H), 6.21 (d, J=5.5 Hz, 1H), 5.80 ("t", J=5.6 Hz, 1H), 5.58 ("t", J=5.1 Hz, 1H), 4.41-4.48 (m, 3H), 2.16 (s, 31), 2.15 (s, 3H), 2.09 (s, 3H); $^{13}$C NMR (125 MHz, CDCl$_3$) δ 170.2, 169.5, 169.4, 154.3, 153.5, 147.4, 142.9, 140.5, 139.2, 133.5, 131.1, 131.0, 128.33, 128.28, 128.17, 127.5, 127.2, 124.1, 86.4, 80.7, 73.2, 70.5, 62.9, 20.8, 20.5, 20.4; HRMS m/z 631.1694 (MNa$^+$[C$_{31}$H$_{28}$ClN$_6$O$_7$Na]=631.1708). Anal. Calcd for C$_{31}$H$_{28}$ClN$_6$O$_7$: C, 59.00; H, 4.31; N, 13.32. Found: C, 58.89; H, 4.45; N, 13.24.

9-(2,3,5-Tri-O-acetyl-β-D-ribofuranosyl)-2-chloro-6-(4,5-diphenylimidazol-1-yl) purine (1.41 g, 1.7 mmol) was dissolved in HOAc (69 mL). To the solution was added AcCl (0.68 mL, 0.75 g, 9.6 mmol), and the mixture was stirred at 65° C. for 60 h in a sealed flask (reaction complete, TLC). Volatiles were evaporated in vacuo, and the residue was washed (CH$_2$Cl$_2$) and dissolved in 0.1 N NaOH/H$_2$O. Precipitation with CO$_2$ gave material (0.41 g, 67%) that was recrystallized (MeOH) to give 2-chloro-6-(4,5-diphenylimidazol-1-yl)purine: mp 277.5-278° C.; UV (MeOH) max 277 nm (∈ 16 100), min 264 nm (∈ 14 800); $^1$H NMR (500 MHz, DMSO-d$_6$) δ 14.04 (s, 1H), 8.84 (s, 1H), 8.73 (s, 1H), 7.20-7.49 (m, 10H); $^{13}$C NMR (125 MHz, DMSO-d$_6$) δ 157.2, 151.6, 147.4, 146.2, 139.7, 139.5, 134.3, 131.3, 131.1, 129.02, 128.98, 128.92, 128.08, 127.8, 127.6, 124.0; HRMS m/z 395.0792 (MNa$^+$[C$_{20}$H$_{13}$ClN$_6$Na]=395.0788). Anal. Calcd for C$_{20}$H$_{13}$ClN$_6$: C, 64.43; H, 3.51; N, 22.54. Found: C, 64.29; H, 3.78; N, 22.53.

Preparation of 2-amino-6-(imidazol-1-yl)purine

Freshly activated guanine (0.45 g, 3 mmol) and (NH$_4$)$_2$SO$_4$ (60 mg) were stirred in HMDS (50 mL) under reflux for 24 h to give a clear solution. Volatiles were evaporated in vacuo, and the residue was dissolved in dried CH$_3$CN (50 mL). Trityl chloride (3.5 g, 12.6 mmol) was added, and the solution was stirred under reflux for 48 h. Volatiles were evaporated in vacuo, and the residue was dissolved in CH$_2$Cl$_2$ (10 mL). NH$_3$/H$_2$O (28-30%, 30 mL) was added, and precipitation was observed immediately. The mixture was stirred at ambient temperature overnight. Volatiles were evaporated in vacuo, and the residue was washed (H$_2$O, CH$_2$Cl$_2$) to give 2-N,9-bistritylguanine as a solid (1.37 g, 72%), which was further purified by dissolving in MeOH/CH$_2$Cl$_2$ (1:15) and filtering: $^1$H NMR (500 MHz, DMSO-d$_6$) δ 10.75 (s, 1H), 7.35 (s, 1H), 7.08-7.19 (m, 19H), 6.87 (d, J=7.4 Hz, 6H), 6.81 (d, J=7.3 Hz, 6H); $^{13}$C NMR (125 MHz, DMSO-d$_6$) δ 157.3, 151.8, 151.0, 145.3, 142.4, 139.6, 129.6, 128.8, 128.5, 128.3, 127.6, 126.9, 120.3, 75.4, 71.1; HRMS m/z 635.2675 (M$^+$[C$_{43}$H$_{33}$N$_5$O]= 635.2685).

A mixture of 2-N,9-bistritylguanine (1.90 g, 3 mmol), I$_2$ (3.88 g, 15 mmol), Ph$_3$P (3.99 g, 15 mmol) and imidazole (1.10 g, 15 mmol) was stirred in toluene (150 mL) at 95° C. for 15 min, and DIPEA (2.9 mL, 2.15 g, 16.6 mmol) was added. The mixture was stirred at 95° C. overnight. After removal of volatiles, the residue was boiled with EtOAc (3×) and filtered hot. The combined EtOAc extracts were evaporated to dryness. The residue was dissolved in TFA/H$_2$O (9:1, 60 mL), and the solution was stirred at 0° C. for 4 h. Volatiles were evaporated in vacuo, and the residue was dissolved in 0.1 N NaOH/H$_2$O//CH$_2$Cl$_2$ (100 mL/100 mL). The organic layer was extracted with 0.1 N NaOH/H$_2$O (50 mL×2), and the aqueous phase was combined, washed [CH$_2$Cl$_2$ (2×50 mL)], and neutralized with CO$_2$. Volatiles were evaporated in vacuo, and the residue was washed (H$_2$O, CH$_2$Cl$_2$) to give 2-amino-6-(imidazol-1-yl)purine (0.40 g, 69%): UV (MeOH) max 222, 320 nm (∈29 800, 8700), min 207, 280 nm (∈ 16 100, 1500); $^1$H NMR (500 MHz, DMSO-d$_6$) δ 12.89 (s, 1H), 8.94 (s, 1H), 8.25 (s, 1H), 8.16 (s, 1H), 7.18 (s, 1H), 6.67 (s, 2H); $^{13}$C NMR (125 MHz, DMSO-d$_6$) δ 160.7, 157.5, 145.4, 141.9, 137.2, 130.5, 117.7, 115.4; HRMS m/z 201.0753 (M$^+$[C$_8$H$_7$N$_7$]=201.0763).

Preparation of 9-(2,3,5-tri-O-benzoyl-β-D-ribofuranosyl)-6-(imidazol-1-yl)purine 6-(Imidazol-1-yl)purine (52 mg, 0.28 mmol) was suspended in a solution of 1-O-acetyl-2,3,5-tri-O-benzoyl-β-D-ribofuranose (160 mg, 0.32 mmol) in dried CH$_3$CN (10 mL). Stannic chloride (0.10 mL, 0.22 g, 0.85 mmol) was added, and the mixture very rapidly became a clear solution. The solution was stirred at ambient temperature for 4 h. NaHCO$_3$ (0.8 g) and H$_2$O (0.1 mL) were added sequentially, and the suspension was stirred for 1 h. The clear solution layer was separated, and the residue was extracted with CH$_3$CN. The extracts and the solution layer were combined, and volatiles were evaporated in vacuo. The residue was chromatographed (CH$_2$Cl$_2$/MeOH, 1:90→1:15) to give 9-(2,3,5-tri-O-benzoyl-β-D-ribofuranosyl)-6-(imidazol-1-yl)purine (179 mg, quantitative): $^1$H NMR (500 MHz, CDCl$_3$) δ 4.72 (dd, J=4.3, 12.2 Hz, 1H), 4.88 (br s, 1H), 4.95 (dd, J=3.0, 12.3 Hz, 1H), 6.29 ("t", J=5.2 Hz, 1H), 6.47-6.50 (m, 2H), 7.24 (s, 1H), 7.35-7.60 (m, 9H), 7.93 (d, J=7.6 Hz, 2H), 8.03 (d, J=7.6 Hz, 2H), 8.07 (d, J=7.6 Hz, 2H), 8.28 (s, 1H), 8.35 (s, 1H), 8.65 (s, 1H), 9.13 (s, 1H); $^{13}$C NMR (125 MHz, CDCCl$_3$) δ 165.0, 164.3, 164.1, 152.1, 151.5, 144.9, 142.2, 136.6, 132.9, 132.8, 132.4, 129.7, 128.8, 128.7, 128.2, 127.5, 127.2, 122.0, 116.3, 86.4, 79.9, 72.9, 70.3, 62.3; HRMS m/z 653.1749 (MNa$^+$ [C$_{34}$H$_{26}$N$_6$O$_7$Na]=653.1761).

Preparation of 9-[2-deoxy-3,5-di-O-(p-toluoyl)-β-D-erythro-pentofuranosyl]-6-(2-propylimidazol-1-yl) purine The sodium salt of 6-(2-propylimidazol-1-yl)purine (55 mg, 0.24 mmol) in dried CH$_3$CN (5 mL) was treated with 2-deoxy-3,5-di-O-(p-toluoyl)-α-D-erythro-pentofuranosyl chloride (0.15 g, 0.39 mmol) in toluene (5 mL) by general method 1. The residue was chromatographed (25 g silica gel, MeOH/CH$_2$Cl$_2$, 1:12) to give the two diastereomers [quantitative, containing traces of α-anomer (α/β ~1:34)]. Recrystallization (EtOAc) gave 9-[2-deoxy-3,5-di-O-(p-toluoyl)-β-D-erythro-pentofuranosyl]-6-(2-propylimidazol-1-yl)purine (68.7 mg, 53%): mp 197-197.5° C.; UV (MeOH) max 242, 276 nm (∈ 31200, 12 500), min 223, 263 nm (∈ 16 400, 9700); $^1$H NMR (500 MHz, CDCl$_3$) δ 8.80 (s, 1H), 8.41 (s, 1H), 8.28 (s, 1H), 8.00 (d, J=8.3 Hz, 2H), 7.89 (d, J=8.3 Hz, 2H), 7.31 (d, J=8.3 Hz, 2H), 7.21 (d, J=8.3 Hz, 2H), 7.12 (s, 1H) 6.65 (dd, J=6.2, 8.1 Hz, 1H), 5.85-5.87 (m, 1H), 4.68-4.83 (m, 3H), 3.30 (t, J=7.3 Hz, 2H), 3.17-3.23 (m, 1H), 2.91-2.95 (m, 1H), 2.47 (s, 3H), 2.39 (s, 3H), 1.85 (sext, J=7.5 Hz, 2H), 1.03 (t, J=7.3 Hz, 3H); NOE difference: irradiation at H1' gave enhancement of the H4' (small), H8 and H2',2" signals; $^{13}$C NMR (125 MHz, CDCl$_3$) δ 166.4, 166.2, 153.1, 152.1, 151.0, 148.1, 144.9, 144.6, 142.4, 130.1, 129.8, 129.6, 129.5, 128.8, 126.8, 126.5, 124.6, 120.8, 85.5, 83.6, 75.2, 64.1, 38.3, 32.8, 22.0, 21.9, 21.5, 14.3; HRMS m/z 603.2347 (MNa$^+$ [C$_{32}$H$_{32}$N$_6$O$_5$Na]=603.2332); Anal. Calcd for C$_{32}$H$_{32}$N$_6$O$_5$: C, 66.20; H, 5.56; N, 14.47. Found: C, 66.59; H, 5.67; N, 14.62.

The reaction was repeated with 6-(2-propylimidazol-1-yl) purine in DMF (342 mg, 1.5 mmol) by general method 1. Volatiles were evaporated in vacuo, and the residue was chromatographed (EtOAc/hexanes~1:1→7:3) to give α-(114 mg) and β-nucleoside (54 mg, contaminated with α-nucleoside, 1:7.3), and a mixture (321 mg, 1:1.3; 56% total, cc/1, 1.14:1).

The α-nucleoside: $^1$H NMR (500 MHz, CDCl$_3$) δ 8.79 (s, 1H), 8.47 (s, 1H), 8.44 (s, 1H), 7.97 (d, J=8.2 Hz, 2H), 7.55 (d, J=8.2 Hz, 2H), 7.29 (d, J=8.0 Hz, 2H), 7.14 (s, 1H), 7.12 (d, J=8.0 Hz, 2H), 6.71 (dd, J=1.5, 7.0 Hz, 1H), 5.71-5.73 (m, 1H), 4.94-4.97 (m, 1H), 4.61-4.68 (m, 2H), 3.30 (t, J=7.3 Hz, 2H), 3.07-3.21 (m, 2H), 2.44 (s, 3H), 2.35 (s, 3H), 1.84 (sext, J=7.5 Hz, 2H), 1.01 (t, J=7.3 Hz, 3H).

Preparation of 2-chloro-9-[2-deoxy-3,5-di-O-(p-toluoyl)-β-D-erythro-pentofuranosyl]-6-(4,5-diphenylimidazol-1-yl)purine The sodium salt of 2-chloro-6-(4,5-diphenylimidazol-1-yl)purine (94 mg, 0.25 mmol) in dried CH$_3$CN (10 mL) was treated with 2-deoxy-3,5-di-O-(p-toluoyl)-α-D-erythro-pentofuranosyl chloride (0.334 g, 0.86 mmol) in CH$_2$Cl$_2$ (10 mL) by general method 2. Sampling of the reaction mixture showed no α-nucleoside by $^1$H NMR (500 MHz). Volatiles were evaporated in vacuo, and the residue was chromatographed (25 g silica gel, EtOAc/hexanes, 3:7→1:1) to give the β-anomer (quantitative). Recrystallization (EtOAc/hexanes) gave 2-chloro-9-[2-deoxy-3,5-di-O-(p-toluoyl)-β-D-erythro-pentofuranosyl]-6-(4,5-diphenylimidazol-1-yl)purine: UV (MeOH) max 240, 275 nm (∈ 53 400, 19 300), min 223, 270 nm (∈ 42 000, 19 100); $^1$H NMR (500 MHz, CDCl$_3$) δ 8.97 (s, 1H), 8.25 (s, 1H), 7.97 (d, J=7.9 Hz, 2H), 7.86 (d, J=7.9 Hz, 2H), 7.55 (d, J=8.2 Hz, 2H), 7.19-7.40 (m, 13H), 6.56 (t, J=7.0 Hz, 1H), 5.77-5.78 (m, 1H), 4.76-4.79 (m, 1H), 4.65-4.69 (m, 2H), 2.92-2.96 (m, 2H), 2.45 (s, 3H), 2.40 (s, 3H); $^{13}$C NMR (125 MHz, CDCl$_3$) δ 166.06, 165.94, 154.03, 153.17, 147.13, 144.71, 144.45, 142.81, 140.38, 139.24, 133.50, 131.02, 129.85, 129.55, 129.37, 129.34, 128.25, 128.17, 127.47, 127.17, 126.41, 126.18, 124.00, 85.11, 83.52, 74.85, 63.84, 38.57, 21.78, 21.71; HRMS m/z 747.2100 (MNa$^+$[C$_{41}$H$_{33}$ClN$_6$O$_5$Na]=747.2099).

Preparation of 6-(2-butylimidazol-1-yl)-2-chloro-9-[2-deoxy-3,5-di-O-(p-toluoyl)-β-D-erythro-pentofuranosyl]purine The sodium salt of 6-(2-butylimidazol-1-yl)-2-chloropurine (0.139 g, 0.5 mmol) in dried CH$_3$CN (10 mL) was treated with 2-deoxy-3,5-di-O-(p-toluoyl)-α-D-erythro-pentofuranosyl chloride (0.334 g, 0.86 mmol) in CH$_2$Cl$_2$ (10 mL) by general method 2. Sampling of the reaction mixture showed traces of α-nucleoside by $^1$H NMR (500 MHz) (1:24). Volatiles were evaporated in vacuo, and the residue was chromatographed (25 g silica gel, EtOAc/hexanes, 3:7→EtOAc) to give the β-anomer (274 mg, 86%) with traces of the α-anomer. Recrystallization (EtOAc/hexanes) gave 6-(2-butylimidazol-1-yl)-2-chloro-9-[2-deoxy-3,5-di-O-(p-toluoyl)-β-D-erythro-pentofuranosyl]purine: UV (MeOH) max 223, 241, 287 nm (∈ 29 900, 33 400, 13 200), min 230, 265 nm (∈ 28 100, 7500); $^1$H NMR (500 MHz, CDCl$_3$) δ 8.51 (s, 1H), 8.26 (s, 1H), 7.98 (d, J=8.0 Hz, 2H), 7.84 (d, J=8.0 Hz, 2H), 7.30 (d, J=8.0 Hz, 2H), 7.19 (d, J=8.0 Hz, 2H), 7.09 (s, 1H), 6.60 (t, J=6.9 Hz, 1H), 5.80 (br s, 1H), 4.78-4.81 (m, 1H), 4.66-4.70 (m, 2H), 3.31 (t, J=7.8 Hz, 2H), 2.97-3.00 (m, 2H), 2.46 (s, 3H), 2.37 (s, 3H), 1.80 (quint, J=7.4 Hz, 2H), 1.50 (sext, J=7.4 Hz, 2H), 0.97 (t, J=7.5 Hz, 3H); $^{13}$C NMR (125 MHz, CDCl$_3$) δ 166.05, 165.98, 154.13, 153.17, 151.43, 147.92, 144.71, 144.39, 142.18, 129.87, 129.53, 129.35, 129.31, 128.91, 126.38, 126.20, 122.70, 120.33, 85.20, 83.57, 74.94, 63.87, 38.61, 30.70, 30.07, 22.64, 21.79, 21.66, 13.91; HRMS 771/z 629.2270 (MH$^+$[C$_{33}$H$_{34}$ClN$_6$O$_5$=629.2279]).

α-Anomer: $^1$H NMR (500 MHz, CDCl$_3$) δ 8.59 (s, 1H), 8.41 (s, 1H), 7.97 (d, J=8.3 Hz, 2H), 7.57 (d, J=8.3 Hz, 2H), 7.30 (d, J=8.0 Hz, 2H), 7.13-7.14 (m, 3H), 6.67 (dd, J=1.8, 6.4 Hz, 1H), 5.72-5.73 (m, 1H), 4.96-4.97 (m, 2H), 4.62-4.70 (m, 2H), 3.31 (t, J=7.8 Hz, 2H), 3.06-3.15 (m, 2H), 2.46 (s, 3H), 2.14 (s, 3H), 1.80 (quint, J=7.4 Hz, 2H), 1.50 (sext, J=7.4 Hz, 2H), 0.97 (t, J=7.3 Hz, 3H).

Preparation of 2-chloro-9-[2-deoxy-3,5-di-O-(p-toluoyl)-β-D-erythro-pentofuranosyl]-6-(2-isopropylimidazol-1-yl)purine The sodium salt of 2-chloro-6-(2-isopropylimidazol-1-yl) purine (0.132 g, 0.5 mmol) in dried CH$_3$CN (10 mL) was treated with 2-deoxy-3,5-di-O-(p-toluoyl)-α-D-erythro-pentofuranosyl chloride (0.334 g, 0.86 mmol) in CH$_2$Cl$_2$ (10 mL) by general method 2 for 1 h (reaction complete, TLC). Sampling of the reaction mixture at the end of the reaction time showed no α-nucleoside by $^1$H NMR (500 MHz). The residue was chromatographed (25 g silica gel, EtOAc/hexanes~1:1) to give 2-chloro-9-[2-deoxy-3,5-di-O-(p-toluoyl)-β-D-erythro-pentofuranosyl]-6-(2-isopropylimidazol-1-yl)purine (quantitative). Recrystallization (EtOAc) gave the compound (0.22 g, 70%): UV (MeOH) max 223, 241, 285 nm (∈ 32 100, 35 400, 14 800), min 230, 265 nm (∈ 30 300, 9200); $^1$H NMR (500 MHz, CDCl$_3$) δ 8.42 (d, J=1.0 Hz, 1H), 8.26 (s, 1H), 7.99 (d, J=7.8 Hz, 2H), 7.85 (d, J=8.3 Hz, 2H), 7.30 (d, J=7.8 Hz, 2H), 7.20 (d, J=8.8 Hz, 2H), 7.11 (d, J=1.0 Hz, 1H), 6.60 (t, J=6.8 Hz, 1H), 5.81 (br s, 1H), 4.78-4.83 (m, 1H), 4.67-4.71 (m, 2H), 4.08 (sept, J=6.8 Hz, 1H), 2.97-3.01 (m, 2H), 2.46 (s, 3H), 2.37 (s, 3H), 1.43 (d, J=6.8 Hz, 3H), 1.41 (d, J=6.8 Hz, 3H); $^{13}$C NMR (125 MHz, CDCl$_3$) δ 166.05, 165.99, 156.18, 154.20, 153.21, 148.15, 144.72, 144.40, 142.25, 129.88, 129.55, 129.36, 129.33, 128.82, 126.44, 126.26, 123.00, 120.38, 85.23, 83.59, 74.93, 63.87, 38.63, 28.81, 21.78, 21.61; HRMS 77/z 637.1931 (MNa$^+$ [C$_{32}$H$_{31}$ClN$_6$O$_5$Na=637.1942]).

This reaction was repeated on a larger scale with the sodium salt of 2-chloro-6-(2-isopropylimidazol-1-yl)purine (902 mg, 3.43 mmol) in dried CH$_3$CN (70 mL) treated with 2-deoxy-3,5-di-O-(p-toluoyl)-α-D-erythro-pentofuranosyl chloride (2.62 g, 6.73 mmol) in CH$_2$Cl$_2$ (70 mL) by general method 2 for 5 h. Sampling of the reaction mixture showed traces of α-nucleoside by $^1$H NMR (500 MHz) (<1:20). Column chromatography (EtOAc/hexanes, 1:1→7:3) gave the β-anomer (quantitative, with traces of α-nucleoside). Recrystallization (EtOAc) gave the β-anomer 2-chloro-9-[2-deoxy-3,5-di-O-(p-toluoyl)-β-D-erythro-pentofuranosyl)-6-(2-isopropylimidazol-1-yl)purine (1.76 g, 84%).

Preparation of 2-chloro-9-[2-deoxy-3,5-di-O-(p-toluoyl)-β-D-erythro-pentofuranosyl]-6-(2-propylimidazol-1-yl)purine The sodium salt of 2-chloro-6-(2-propylimidazol-1-yl)purine (0.13 g, 0.5 mmol) in dried $CH_3CN$ (10 mL) was treated with 2-deoxy-3,5-di-O-(p-toluoyl)-α-D-erythro-pentofuranosyl chloride (0.30 g, 0.8 mmol) in $CH_2Cl_2$ (10 mL) by general method 2. No α-nucleoside was detected by $^1H$ NMR. Column chromatography was performed twice (25 g silica gel, $MeOH/CH_2Cl_2$, 1:30, and EtOAc/hexanes, 1:1) to give 2-chloro-9-[2-deoxy-3,5-di-O-(p-toluoyl)-β-D-erythro-pentofuranosyl]-6-(2-propylimidazol-1-yl)purine (0.26 g, 83%), which was recrystallized (EtOAc) to give analytically pure material (0.17 g, 55%): mp 192-193° C.; UV (MeOH) max 220, 239, 287 nm ($\in$ 40 700, 38 300, 16 700), min 231, 265 nm ($\in$ 35 900, 10 300); $^1H$ NMR (500 MHz, $CDCl_3$) δ 8.52 (s, 1H), 8.27 (s, 1H), 8.00 (d, J=7.8 Hz, 2H), 7.86 (d, J=7.8 Hz, 2H), 7.32 (d, J=7.8 Hz, 2H), 7.28 (d, J=7.8 Hz, 2H), 7.20 (s, 1H), 6.61 (t, J=7.1 Hz, 1H), 5.82-5.83 (m, 1H), 4.84-4.68 (m, 3H), 3.29 (t, J=7.8 Hz, 2H), 2.98-3.01 (m, 2H), 2.47 (s, 3H), 2.38 (s, 3H), 1.86 (sext, J=7.5 Hz, 2H), 1.07 (t, J=7.3 Hz, 3H); NOE difference: H1' was irradiated, and enhancement of H4' (small), H8 and H2',2" signals was observed; $^{13}C$ NMR (125 MHz, $CDCl_3$) δ 166.29, 166.23, 154.38, 153.42, 151.47, 148.18, 144.97, 144.65, 142.40, 130.12, 129.78, 129.61, 129.56, 129.20, 126.63, 126.44, 122.95, 120.57, 85.46, 83.82, 75.19, 64.12, 38.88, 33.12, 22.03, 21.91, 21.60, 14.25; HRMS m/z 637.1940 ($MNa^+$ $[C_{32}H_{31}ClN_6O_5Na=637.1942]$). Anal. Calcd for $C_{32}H_{31}ClN_6O_5$: C, 62.49; H, 5.08; N, 13.66. Found: C, 62.44; H, 5.18; N, 13.72.

This reaction was repeated on a larger scale with the sodium salt of 2-chloro-6-(2-propylimidazol-1-yl)purine (1.54 g, 5.87 mmol) in dried $CH_3CN$ (100 mL) treated with 2-deoxy-3,5-di-O-(p-toluoyl)-α-D-erythro-pentofuranosyl chloride (3.74 g, 9.62 mmol) in $CH_2Cl_2$ (100 mL) by general method 2 for 5 h (reaction complete, TLC). Sampling at different reaction times showed no α-nucleoside by $^1H$ NMR (500 MHz). Volatiles were evaporated, and the residue was dissolved in $CH_2Cl_2$. The solution was washed ($H_2O$) and dried ($Na_2SO_4$), and volatiles were evaporated in vacuo. The residue was chromatographed (EtOAc/hexanes, 1:1→7:3) to give 2-chloro-9-[2-deoxy-3,5-di-O-(p-toluoyl)-β-D-erythro-pentofuranosyl]-6-(2-propylimidazol-1-yl)purine (3.42 g, 95%). Recrystallization from EtOAc gave the β-anomer (2.75 g, 76%).

Preparation of 3-benzyl-1-{2-chloro-9-[2-deoxy-3,5-di-O-(p-toluoyl)-β-D-erythro-pentofuranosyl]purin-6-yl}-2-propylimidazolium iodide 2-Chloro-9-[2-deoxy-3,5-di-O-(p-toluoyl)-β-D-erythro-pentofuranosyl]-6-(2-propylimidazol-1-yl)purine (0.615 g, 1 mmol) was treated with a solution of BnI in $CH_3CN$ (0.3 M, 40 mL, 12 mmol) by method 3 to give 3-benzyl-1-{2-chloro-9-[2-deoxy-3,5-di-O-(p-toluoyl)-β-D-erythro-pentofuranosyl]purin-6-yl}-2-propylimidazolium iodide (0.83 g, crude): $^1H$ NMR (500 MHz, $CDCl_3$) δ 8.94 (s, 1H), 8.49 (s, 1H), 8.00 (d, J=8.5 Hz, 2H), 7.88 (d, J=8.0 Hz, 2H), 7.81 (s, 1H), 7.46-7.50 (m, 5H), 7.32 (d, J=8.0 Hz, 2H), 7.25 (d, J=8.0 Hz, 2H), 6.67 (t, J=7.3 Hz, 1H), 5.75-5.85 (m, 3H), 4.71-4.82 (m, 3H), 3.67-3.74 (m, 2H), 2.99-3.02 (m, 2H), 2.47 (s, 3H), 2.42 (s, 3H), 1.75-1.81 (m, 2H), 1.17 (t, J=7.5 Hz, 3H); HRMS m/z 705.2606 ($M^+[C_{39}H_{38}ClN_6O_5=705.2592]$).

Preparation of 6-amino-2-chloro-9-(2-deoxy-β-D-erythro-pentofuranosyl)purine (2-chloro-2'-deoxyadenosine) (cladribine)

Treatment of 3-benzyl-1-{2-chloro-9-[2-deoxy-3,5-di-O-(p-toluoyl)-β-D-erythro-pentofuranosyl]purin-6-yl}-2-propylimidazolium iodide (0.83 g, crude) with $NH_3/MeOH$ (26%, 50 mL) at 60° C. followed by ion exchange chromatography (Dowex 1×2 [$OH^-$], $H_2O/MeOH$) by method 3 gave cladribine (0.31 g, quantitative). Recrystallization from EtOH gave a white solid (0.153 g, 54%), and the residue from the mother liquor was recrystallized from $H_2O$ to give a second crop (0.015 g, 59% total): mp>300° C.; UV (MeOH) max 212, 265 nm ($\in$ 24 000, 14 600), min 229 nm ($\in$ 2000); $^1H$ NMR (500 MHz, DMSO-$d_6$) δ 8.36 (s, 1H), 7.83 (br, 2H), 6.26 (t, J=6.7 Hz, 1H), 5.32 (d, J=4.3 Hz, 1H), 4.97 (t, J=5.5 Hz, 1H), 4.38 (s, 1H), 3.85 (s, 1H), 3.57-3.61 (m, 1H), 3.48-3.53 (m, 1H), 2.62-2.67 (m, 1H), 2.25-2.29 (m, 1H); $^{13}C$ NMR (125 MHz, DMSO-$d_6$) δ 157.5, 153.6, 150.8, 140.5, 118.8, 88.6, 84.2, 71.4, 62.3, 38.0; HRMS m/z 285.0615 ($M^+$ $[C_{10}H_{12}ClN_5O_3]=285.0629$). Anal. Calcd for $C_{10}H_{12}ClN_5O_3$: C, 42.04; H, 4.23; N, 24.51. Found: C, 41.87; H, 4.50; N, 24.39.

Preparation of 6-amino-2-chloro-9-(2-deoxy-β-erythropentofuranosyl)purine (2-chloro-2'-deoxyadenosine) (cladribine)

A solution of 2-chloro-9-[2-deoxy-3,5-di-O-(p-toluoyl)-β-D-erythro-pentofuranosyl]-6-(2-pentylimidazol-1-yl)purine (0.35 g, 0.55 mmol) in methanolic ammonia (14%) was stirred at 80° C. for 13 h. Volatiles were evaporated, and the oily residue was extracted with $CH_2Cl_2$ (10 mL) to remove lipophilic by-products. The semi-solid residue was dissolved in acetone (with additions of small amounts of MeOH—if necessary), volatiles were evaporated, and the semi-solid was allowed to crystallize (~1 h). This material was extracted with $CH_2Cl_2$ (10 mL) and dried. The resulting 2-chloro-2'-deoxyadenosine (white powder; 113 mg, 70%) was pure by $^1H$ NMR analysis. Additional amounts of cladribine (~24 mg, 15%; containing traces of the α-anomer) were recovered from the concentrated extracts by chromatography (EtOAc→EtOAc/MeOH, 10:1) followed by a similar extraction sequence.

What is claimed is:

1. A method for preparing an N-9 purine nucleoside, comprising:
    (a) glycosylating a 6-(azolyl)purine at the N-9 position; and,
    (b) displacing the 6-(azolyl) group from the glycosylate from step (a) with a nucleophile to yield an N-9 purine nucleoside.

2. A method for preparing an N-9 purine nucleoside, comprising:
    (a) introducing an (azolyl) group at the 6 position of a purine;
    (b) glycosylating the purine product from step (a) at the N-9 position; and,
    (c) displacing the 6-(azolyl) group from step (a) with a nucleophile to yield an N-9 purine nucleoside.

3. A method for preparing an N-9 purine nucleoside comprising:

(a) contacting a 6-(azolyl)-substituted purine of Formula I

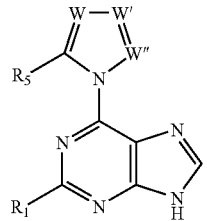

with a glycosylating agent in the presence of a base, where each W, W' and W" is independently selected from —N—, —CH— and $CR_2$;

$R_1$, $R_2$, and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl;

(b) alkylating the appended 6-(azolyl) ring on the 6-substituted purine nucleoside from step (a);

(c) contacting the alkylated 6-substituted purine nucleoside from step (b) with ammonia to obtain a nucleoside of Formula III

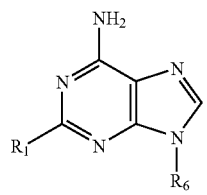

where $R_6$ is a glycosyl group.

4. A method for preparing an N-9 purine nucleoside comprising:

(a) contacting a 6-(imidazol-1-yl)purine of Formula XV

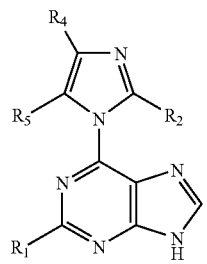

with a glycosylating agent in the presence of a base, where $R_1$, $R_2$, $R_4$, and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl;

(b) alkylating the appended 6-(imidazol-1-yl) ring on the 6-substituted purine nucleoside from step (a);

(c) contacting the alkylated 6-(imidazol-1-yl)-substituted purine nucleoside from step (b) with ammonia to obtain a nucleoside of Formula III

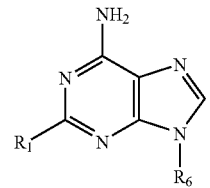

where $R_6$ is a glycosyl group.

5. A method for preparing an N-9 purine nucleoside comprising:

(a) contacting a 6-(1,2,4-triazol-4-yl)-substituted purine of Formula XXII

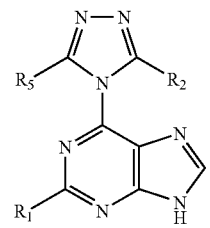

with a glycosylating agent in the presence of a base, where $R_1$, $R_2$, and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl;

(b) alkylating the appended 6-(1,2,4-triazol-4-yl) ring on the 6-substituted purine nucleoside from step (a);

(c) contacting the alkylated 6-(1,2,4-triazol-4-yl)-substituted purine nucleoside from step (b) with ammonia in a third solvent to obtain a nucleoside of Formula III

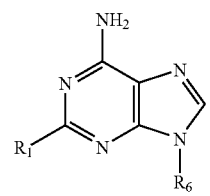

where $R_6$ is a glycosyl group.

6. A method for preparing 2-chloro-2'-deoxyadenosine (2-CdA, cladribine) comprising:

(a) contacting a compound having Formula XXVIII

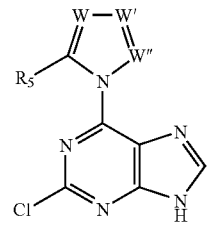

where each W, W' and W" is independently selected from —N—, —CH— and $CR_2$, each of $R_2$ and $R_5$ is independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl, with a base in a first polar solvent followed by contacting an activated and hydroxyl-protected 2-deoxy-α-D-erythro-pentofuranosyl compound in a second less polar solvent to form a glycosylate product;

(b) contacting the glycosylate product from step (a) with ammonia in a third solvent to obtain 2-CdA.

7. A method for preparing 2-chloro-2'-deoxyadenosine (2-CdA, cladribine) comprising:

(a) contacting a compound having Formula XXVIII

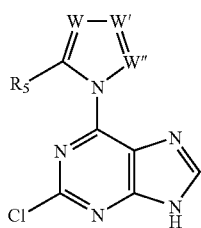

where each W, W' and W'' is independently selected from —N—, —CH— and $CR_2$, each of $R_2$ and $R_5$ is independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl, with a base in a first polar solvent followed by contacting an activated and hydroxyl-protected 2-deoxy-α-D-erythro-pentofuranosyl compound in a second less polar solvent to form a glycosylate product;

(b) alkylating the appended 6-(azolyl) ring on the 6-substituted purine nucleoside from step (a);

(c) contacting the alkylated glycosylate product from step (b) with ammonia in a third solvent to obtain 2-CdA.

8. A method for preparing 2-CdA (cladribine) comprising:

(a) contacting a compound having Formula XXIX

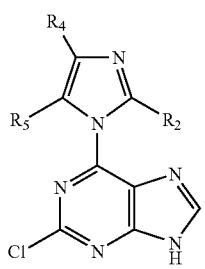

where each of $R_2$, $R_4$, and $R_5$ is independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl, with a base in a first polar solvent followed by contacting an activated and hydroxyl-protected 2-deoxy-α-D-erythro-pentofuranosyl compound in a second less polar solvent to form a glycosylate product;

(b) contacting the glycosylate product from step (a) with ammonia in a third solvent to obtain 2-CdA.

9. A method for preparing 2-CdA (cladribine) comprising:

(a) contacting a compound having Formula XXIX

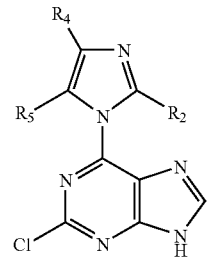

where $R_2$, $R_4$, and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl, with a base in a first polar solvent followed by contacting an activated and hydroxyl-protected 2-deoxy-α-D-erythro-pentofuranosyl compound in a second less polar solvent to form a glycosylate product;

(b) alkylating the appended 6-(imidazol-1-yl) ring on the 6-substituted purine nucleoside from step (a);

(c) contacting the alkylated glycosylate product from step (b) with ammonia in a third solvent to obtain 2-CdA.

10. A method for preparing 2-CdA (cladribine) comprising:

(a) contacting a compound having Formula XXX

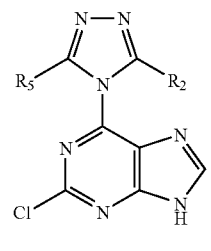

where $R_2$ and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl, with a base in a first polar solvent followed by contacting an activated and hydroxyl-protected 2-deoxy-α-D-erythro-pentofuranosyl compound in a second less polar solvent to form a glycosylate product;

(b) contacting the glycosylate product from step (a) with ammonia in a third solvent to obtain 2-CdA.

11. A method for preparing 2-CdA (cladribine) comprising:

(a) contacting a compound having Formula XXX where $R_2$ and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl, with a base in a first polar solvent followed by contacting an activated and hydroxyl-protected 2-deoxy-α-D-erythro-pentofuranosyl compound in a second less polar solvent to form a glycosylate product;

(b) alkylating the appended 6-(1,2,4-triazol-4-yl) ring on the 6-substituted purine nucleoside from step (a);

(c) contacting the alkylated glycosylate product from step (b) with ammonia in a third solvent to obtain 2-CdA.

12. The method according to any of claims 6-11 wherein the first polar solvent is a solvent mixture with an average dielectric constant of between about 5 and about 40.

13. The method according to claim 12 wherein the first polar solvent has an average dielectric constant of about 20.

14. The method according to any of claims 6-11 wherein the base is selected from the group consisting of sodium hydride, potassium hydride, sodium carbonate, potassium carbonate, and potassium hexamethyldisilazide.

15. A method for preparing a 6-(azolyl)-substituted purine, comprising:

(a) introducing an azolyl ring at the 6 position of a purine nucleoside;

(b) cleaving the glycosidic bond of the nucleoside from step (a) to yield a 6-(azolyl)purine.

16. A method for preparing a purine of Formula I

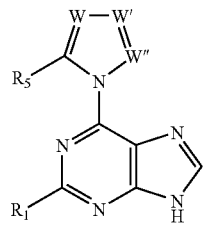

where each W, W' and W" is independently selected from —N—, —CH— and $CR_2$;

$R_1$, $R_2$ and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl;

comprising contacting a compound of Formula XXXI:

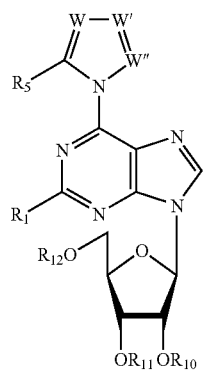

where $R_{10}$, $R_{11}$, and $R_{12}$ are hydroxyl protecting groups, with a deglycosylation agent.

17. A method for preparing a purine of Formula XV

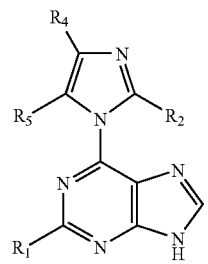

where $R_1$, $R_2$, $R_4$, and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl;

comprising contacting a compound of Formula XXXII

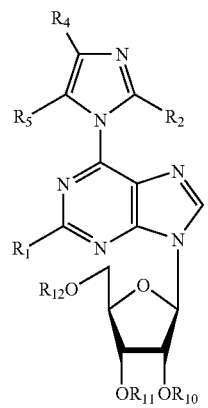

where $R_{10}$, $R_{11}$, and $R_{12}$ are hydroxyl protecting groups, with a deglycosylation agent.

18. A method for preparing a purine of Formula XXII

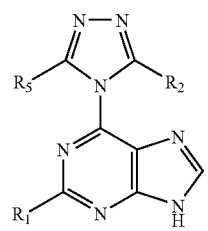

where $R_1$, $R_2$ and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl;

comprising contacting a compound of Formula XXXIII

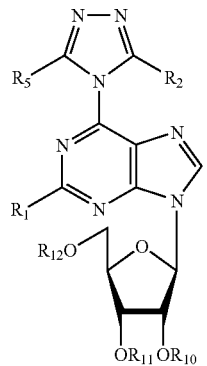

where $R_{10}$, $R_{11}$, and $R_{12}$ are hydroxyl protecting groups, with a deglycosylation agent.

19. A compound of Formula I

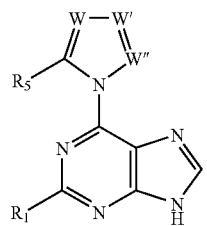

where each W, W' and W" is independently selected from —N—, —CH— and $CR_2$;
at least one of W, W' and W" is —N—;
$R_1$, $R_2$, and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl;
and pharmaceutically acceptable salts of these compounds, provided that:
(1) when $R_1$ is amino and both W and W' are N, then $R_5$ is not hydrogen;
(2) when $R_1$ is hydrogen and W' and W" are CH, then $R_5$ is not hydrogen;
(3) when $R_1$ is hydrogen and $R_5$ is methyl, then W' and W" are not CH;
(4) when $R_1$ and $R_5$ are hydrogen and W' is $CCH_3$, then W" is not CH;
(5) when $R_1$ and $R_5$ are hydrogen and W' is CH, then W" is not N;
(6) when $R_1$ and $R_5$ are hydrogen and W" is N, then W and W' are not CH;
(7) when $R_1$ and $R_5$ are hydrogen and W" is N, then W is not $CCH_3$;
(8) when $R_1$ and $R_5$ are hydrogen and W" is N, then W' is not $CCH_3$;
(9) when $R_1$ and $R_5$ are hydrogen and W" is CH then W and W' are not N.

20. A compound of Formula XV

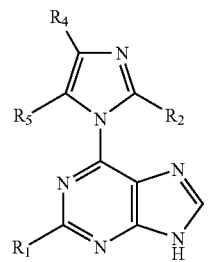

where $R_1$, $R_2$, $R_4$, and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl;
and pharmaceutically acceptable salts of these compounds, provided that:
(1) when $R_1$, $R_2$ and $R_4$ are hydrogen, then $R_5$ is not hydrogen;
(2) when $R_1$, $R_2$ and $R_5$ are hydrogen, then $R_4$ is not methyl;
(3) when $R_1$, $R_4$ and $R_5$ are hydrogen, then $R_2$ is not methyl.

21. A compound of Formula XXII

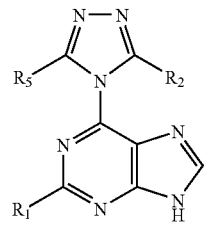

where $R_1$, $R_2$ and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl;
and pharmaceutically acceptable salts of these compounds, provided that when $R_1$ is amino or hydrogen, then at least one of $R_2$ and $R_5$ is not hydrogen.

22. A compound of Formula XXXVI

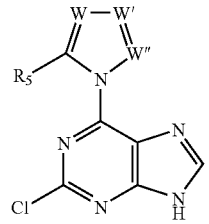

where each W, W' and W" is independently selected from —N—, —CH— and $CR_2$;
at least one of W, W' and W" is —N—;
$R_2$ and $R_5$ are independently selected from hydrogen, $C_{1-10}$ alkyl, $C_{1-10}$ alkoxy, $C_{1-10}$ alkylthio, halogen, amino, $C_{1-10}$ alkylamino, di-$C_{1-10}$ alkylamino, $C_{1-10}$ acylamino, aryl, and heteroaryl;
and pharmaceutically acceptable salts of these compounds.

* * * * *